US010087218B2

(12) United States Patent
Bock

(10) Patent No.: US 10,087,218 B2
(45) Date of Patent: *Oct. 2, 2018

(54) VACCINE ANTIGENS THAT DIRECT IMMUNITY TO CONSERVED EPITOPES

(71) Applicant: UNIVERSITY OF UTAH RESEARCH FOUNDATION, Salt Lake City, UT (US)

(72) Inventor: Susan C. Bock, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/331,513

(22) Filed: Oct. 21, 2016

(65) Prior Publication Data

US 2017/0267729 A1   Sep. 21, 2017

Related U.S. Application Data

(62) Division of application No. 13/993,862, filed as application No. PCT/US2011/064442 on Dec. 12, 2011, now Pat. No. 9,512,182.

(60) Provisional application No. 61/626,792, filed on Oct. 3, 2011, provisional application No. 61/457,028, filed on Dec. 13, 2010.

(51) Int. Cl.
| | |
|---|---|
| C07K 14/005 | (2006.01) |
| A61K 39/12 | (2006.01) |
| A61K 39/145 | (2006.01) |
| A61K 39/00 | (2006.01) |

(52) U.S. Cl.
CPC ............ *C07K 14/005* (2013.01); *A61K 39/12* (2013.01); *A61K 39/145* (2013.01); *A61K 2039/55566* (2013.01); *A61K 2039/58* (2013.01); *C12N 2760/16034* (2013.01); *C12N 2760/16122* (2013.01); *C12N 2760/16134* (2013.01)

(58) Field of Classification Search
CPC ........... C12N 2760/16134; C12N 2760/16122; C12N 7/00; C12N 2760/16034; C12N 2760/16071; C12N 2760/16022; C12N 2760/16162; C12N 2760/16111; C12N 2760/16121; A61K 39/12; A61K 39/145; A61K 2300/00; A61K 39/39; A61K 2039/55561; A61K 39/00; A61K 2039/55566; A61K 9/0019; A61K 35/76; C07K 14/005; C07K 16/1018; G01N 33/56983; G01N 2333/11

See application file for complete search history.

(56) References Cited

U.S. PATENT DOCUMENTS

| | | | |
|---|---|---|---|
| 5,585,250 A | 12/1996 | Garrity et al. | |
| 5,853,724 A | 12/1998 | Garrity et al. | |
| 2008/0032921 A1 | 2/2008 | Alexander et al. | |
| 2009/0162383 A1 | 6/2009 | Padlan | |
| 2010/0061990 A1 | 3/2010 | Sasisekharan et al. | |
| 2011/0177121 A1 | 7/2011 | Nara et al. | |
| 2013/0315929 A1 | 11/2013 | Bock | |
| 2014/0004149 A1 | 1/2014 | Tobin et al. | |

OTHER PUBLICATIONS

Tobin GJ, Trujillo JD, Bushnell RV, Lin G, Chaudhuri AR, Long J, Barrera J, Pena L, Grubman MJ, Nara PL. Deceptive imprinting and immune refocusing in vaccine design. Vaccine. Nov. 18, 2008;26(49):6189-99. Epub Oct. 11, 2008.*
Li J, Wang Y, Liang Y, Ni B, Wan Y, Liao Z, Chan KH, Yuen KY, Fu X, Shang X, Wang S, Yi D, Guo B, Di B, Wang M, Che X, Wu Y. Fine antigenic variation within H5N1 influenza virus hemagglutinin's antigenic sites defined by yeast cell surface display. Eur J Immunol. Dec. 2009;39(12):3498-510.*
Tangri S, Mothé BR, Eisenbraun J, Sidney J, Southwood S, Briggs K, Zinckgraf J, Bilsel P, Newman M, Chesnut R, Licalsi C, Sette A. Rationally engineered therapeutic proteins with reduced immunogenicity. J Immunol. Mar. 15, 2005;174(6):3187-96.*
Thomas PG, Brown SA, Keating R, Yue W, Morris MY, So J, Webby RJ, Doherty PC. Hidden epitopes emerge in secondary influenza virus-specific CD8+ T cell responses. J Immunol. Mar. 1, 2007;178(5):3091-8.*
Andreansky SS, Stambas J, Thomas PG, Xie W, Webby RJ, Doherty PC. Consequences of immunodominant epitope deletion for minor influenza virus-specific CD8+-T-cell responses. J Virol. Apr. 2005;79(7):4329-39.*
Ruckwardt TJ, Luongo C, Malloy AM, Liu J, Chen M, Collins PL, Graham BS. Responses against a subdominant CD8+ T cell epitope protect against immunopathology caused by a dominant epitope. J Immunol. Oct. 15, 2010;185(8):4673-80. Epub Sep. 10, 2010.*
Welsh RM, Fujinami RS. Pathogenic epitopes, heterologous immunity and vaccine design. Nat Rev Microbiol, Jul. 2007; 5(7):, Jul. 5, 2007, 555-63.
U.S. Appl. No. 13/993,862, Response to Restriction/Election Requirement, dated Aug. 26, 2014.
U.S. Appl. No. 13/993,862, Notice of Allowance and Fees Due, dated Jul. 22, 2016.
U.S. Appl. No. 13/993,862, Non-Final Office Action, dated Dec. 30, 2015.
U.S. Appl. No. 13/993,862, Response to Non-Final Office Action, dated Feb. 18, 2015.
U.S. Appl. No. 13/993,862, Restriction/Election Requirement, dated Jul. 11, 2014.
U.S. Appl. No. 13/993,862, Final Office Action, dated May 21, 2015.
U.S. Appl. No. 13/993,862, Response to Final Office Action, dated Nov. 23, 2015, 1-12.

(Continued)

*Primary Examiner* — Rachel B Gill
(74) *Attorney, Agent, or Firm* — Stoel Rives LLP

(57) ABSTRACT

A method of identification and elimination of immunodominant epitopes to elicit a response to secondary epitopes, especially conserved structures, is described, and applied to influenza haemagglutinin (HA). Identification of the primary epitopes in (HA), and replacement of amino acids having high LODrps with corresponding low LODrps amino acids produces an HA molecule which induces antibody responses to conserved HA residues. Modified HA molecules induce a broadly neutralizing vaccine.

15 Claims, 10 Drawing Sheets

Specification includes a Sequence Listing.

(56) References Cited

OTHER PUBLICATIONS

U.S. Appl. No. 13/993,862, Non-Final Office Action, dated Sep. 18, 2014.

Andersen, et al., "Predicition of Residues in Discontinuous B-Cell Epitopes Using Protein 3D Structures", Protein Science vol. 15, Cold Spring Harbor Laboratory Press, The Protein Society 2006, 2006, 2558-2567.

Chaichoun, et al., Hemagglutinin [Influenza A virus (A/openbill stork/Thailand/VSMU-6-BKK/2004(H5N1))]. GenBank Acc. No. ADK22450., Jul. 31, 2011.

El-Manzalawy, "Recent Advances in B-Cell Epitope Predicition Methods", Immunome Research, 6 (Suppl 2):52, 2010, 1-9.

Wang, et al., "Identification of the progenirots of Indonesian and Vietnamese avian influenza A (H5N1) viruses from southern China", J. Virol.;82(7) doi: 10.1128/JVI.02468-07. Epub Jan. 23, 2008, Apr. 2008, 3405-14.

Kaverin, et al., "Influenza A Virus (A/Viet Nam/1203/2004(H5N1))", NCBI GenBank Dep. No. ABW90129. Acc., Nov. 14, 2007.

Nagata, et al., "Removal of B Cell Epitopes as a practical approach for reducing the immunogenicity of foreign protein-based therapeutics", Advanced Drug Delivery Review 61, 2009, 997-983.

PCTUS2011064442, International Search Report and Written Opinion, dated Apr. 13, 2012.

Ponomarenko, et al., "B-Cell Epitope Predicition", Structural Bioinformatics, Second Edition, John Wiley & Sons, 2009, 849-880.

Rudneva, et al., "Influenza A virus (A/Viet Nam/1203/2004(H5N1))", NCBI GenBank Acc. No. AII30337. Dep. Aug. 9, 2014.

Van Der Werf, "Hemagglutinin, partial [Influenza A virus (A/chicken/Cambodia/1/2004(H5N1))]", GenBank Acc. No. ABO30353, Dep., May 1, 2008.

Wang, et al., Hemagglutinin, partial [Influenza A virus (A/chicken/Yunnan/1215/2002(H5N1))]. GenBank Acc. No. ACA47945., Mar. 18, 2008.

\* cited by examiner

Fig. 2 metallothioein promoter | HA1 | HA2 | foldon
BiP signal peptide | Xho I | | BspE I | His.6
Xba I | Avr II | Spe I | Mlu I pMT-BIP-V1203.HA-foldon-His.6

```
>xHA.par (V1203 parental)(SEQ ID NO:1)
Met Lys Leu Cys Ile Leu Leu Ala Val Val Ala Phe Val Gly Leu Ser Leu Gly
RSDQICIGYHANNSTEQVDTIMEKNVTVTHAQDILEKKHNGKLCDLDGVKPLILRDCSVA
GWLLGNPMCDEFINVPEWSYIVEKANPVNDLCYPGDFNDYEELKHLL
SRINHFEKIQIIPKSSWSSHEASLGVSSACPYQGKSSFFRNVVWLIKKNSTYPTIKRSYN
NTNQEDLLVLWGIHHPNDAAEQTKLYQNPTTYISVGT
STLNQRLVPRIATRSKVNGQSGRMEFFWTILKPNDA
INFESNGNFIAPEYAYKIVKKGDSTIMKSELEYGNCNTKCQTPMGAINSSMPFHNIHPLT
IGECPKYVKSNRLVLATGLRNSPQRETRGLFGAIAGFIEGGWQGMVDGWYGYHHSNEQGS
GYAADKESTQKAIDGVTNKVNSIIDKMNTQFEAVGREFNNLERRIENLNKKMEDGFLDVW
TYNAELLVLMENERTLDFHDSNVKNLYDKVRLQLRDNAKELGNGCFEFYHKCDNECMESV
RNGTYDYPQYSEEARLKREEISS
GRLVPRGSPGSGYIPEAPRDGQAYVRKDGEWVLLSTFLTGHHHHH*

>xHA.em (escape mutant substitutions)(SEQ ID NO:2)
Met Lys Leu Cys Ile Leu Leu Ala Val Val Ala Phe Val Gly Leu Ser Leu Gly
RSDQICIGYHANNSTEQVDTIMEKNVTVTHAQDILEKKHNGKLCDLDGVKPLILRDCSVA
GWLLGNPMCDEFINVPEWSYIVEKANPVNDLCYPGDFNDYEELKHLL
SRINHFEKIQIIPKSYWSDHNASLGVSSACLYKEEFSFFRNVVWLTEKNSAYPTIKGSYN
NTNQEDLLVLWGIHHPNDAAEQTELYQNPTTYISVGT
STLNQRLVPRIATRSKVNGQSGRMEFFWTILKPNDA
INFESNGNFIAPEYAYKIVKKGDSTIMKSELEYGNCNTKCQTPMGAINSSMPFHNIHPLT
IGECPKYVKSNRLVLATGLRNSPQRETRGLFGAIAGFIEGGWQGMVDGWYGYHHSNEQGS
GYAADKESTQKAIDGVTNKVNSIIDKMNTQFEAVGREFNNLERRIENLNKKMEDGFLDVW
TYNAELLVLMENERTLDFHDSNVKNLYDKVRLQLRDNAKELGNGCFEFYHKCDNECMESV
RNGTYDYPQYSEEARLKREEISS
GRLVPRGSPGSGYIPEAPRDGQAYVRKDGEWVLLSTFLTGHHHHH*

>xHA.1(SEQ ID NO:3)
Met Lys Leu Cys Ile Leu Leu Ala Val Val Ala Phe Val Gly Leu Ser Leu Gly
RSDQICIGYHANNSTEQVDTIMEKNVTVTHAQDILEKKHNGKLCDLDGVKPLILRDCSVA
GWLLGNPMCDEFINVPEWSYIVEKANPVNDLCYPGDFNDYEELKHLL
SRINHFEKIQIIPKSSWSSHEASLGVSSACPYQGTASFFRNVVWLIKKNSTYPTIKRSYN
NTNQEDLLVLWGIHHPNDAAEQTKLYQNPTTYISVGT
STLNQRLVPRIATRSKVNGQSGRMEFFWTILKPNDA
INFESNGNFIAPEYAYKIVKKGDSTIMKSELEYGNCNTKCQTPMGAINSSMPFHNIHPLT
IGECPKYVKSNRLVLATGLRNSPQRETRGLFGAIAGFIEGGWQGMVDGWYGYHHSNEQGS
GYAADKESTQKAIDGVTNKVNSIIDKMNTQFEAVGREFNNLERRIENLNKKMEDGFLDVW
TYNAELLVLMENERTLDFHDSNVKNLYDKVRLQLRDNAKELGNGCFEFYHKCDNECMESV
RNGTYDYPQYSEEARLKREEISS
GRLVPRGSPGSGYIPEAPRDGQAYVRKDGEWVLLSTFLTGHHHHH*
```

*FIG. 4*

>xHA.2 (SEQ ID NO:4)
Met Lys Leu Cys Ile Leu Leu Ala Val Val Ala Phe Val Gly Leu Ser Leu Gly
RSDQICIGYHANNSTEQVDTIMEKNVTVTHAQDILEKKHNGKLCDLDGVKPLILRDCSVA
GWLLGNPMCDEFINVPEWSYIVEKANPVNDLCYPGDFNDYEELKHLL
*SRINHFEKIQIIPKSAWSSHEASLGVSSACPYQGKSSFFRNVVWLIKKNSTYPTIKTSYN
NTNQEDLLVLWGIHHPNDAAEQTKLYQNPTTYISVGT*
STLNQRLVPRIATRSKVNGQSGRMEFFWTILKPNDA
INFESNGNFIAPEYAYKIVKKGDSTIMKSELEYGNCNTKCQTPMGAINSSMPFHNIHPLT
IGECPKYVKSNRLVLATGLRNSPQRETRGLFGAIAGFIEGGWQGMVDGWYGYHHSNEQGS
GYAADKESTQKAIDGVTNKVNSIIDKMNTQFEAVGREFNNLERRIENLNKKMEDGFLDVW
TYNAELLVLMENERTLDFHDSNVKNLYDKVRLQLRDNAKELGNGCFEFYHKCDNECMESV
RNGTYDYPQYSEEARLKREEISS
GRLVPRGSPGSGYIPEAPRDGQAYVRKDGEWVLLSTFLTGHHHHHH*

>xHA.3 (SEQ ID NO:5)
Met Lys Leu Cys Ile Leu Leu Ala Val Val Ala Phe Val Gly Leu Ser Leu Gly
RSDQICIGYHANNSTEQVDTIMEKNVTVTHAQDILEKKHNGKLCDLDGVKPLILRDCSVA
GWLLGNPMCDEFINVPEWSYIVEKANPVNDLCYPGDFNDYEELKHLL
*SRINHFEKIQIIPKSSWSSHEASLGVSSACPYQGKSSFFRNVVWLIAKNSTYPTIKRSYN
NTNQEDLLVLWGIHHPNDAAEQTKLYQNPTTYISVGT*
STLNQRLVPRIATRSKVNGQSGRMEFFWTILKPNDA
INFESNGNFIAPEYAYKIVKKGDSTIMKSELEYGNCNTKCQTPMGAINSSMPFHNIHPLT
IGECPKYVKSNRLVLATGLRNSPQRETRGLFGAIAGFIEGGWQGMVDGWYGYHHSNEQGS
GYAADKESTQKAIDGVTNKVNSIIDKMNTQFEAVGREFNNLERRIENLNKKMEDGFLDVW
TYNAELLVLMENERTLDFHDSNVKNLYDKVRLQLRDNAKELGNGCFEFYHKCDNECMESV
RNGTYDYPQYSEEARLKREEISS
GRLVPRGSPGSGYIPEAPRDGQAYVRKDGEWVLLSTFLTGHHHHHH*

>xHA.4a (SEQ ID NO:6)
Met Lys Leu Cys Ile Leu Leu Ala Val Val Ala Phe Val Gly Leu Ser Leu Gly
RSDQICIGYHANNSTEQVDTIMEKNVTVTHAQDILEKKHNGKLCDLDGVKPLILRDCSVA
GWLLGNPMCDEFINVPEWSYIVEKANPVNDLCYPGDFNDYEELKHLL
*SRINHFEKIQIIPKSSWSSHEASLGVSSACLYKGESSFFRNVVWLIEKNSTYPTIKGSYN
NTNQEDLLVLWGIHHPNDAAEQTELYQNPTTYISVGT*
STLNQRLVPRIATRSKVNGQSGRMEFFWTILKPNDA
INFESNGNFIAPEYAYKIVKKGDSTIMKSELEYGNCNTKCQTPMGAINSSMPFHNIHPLT
IGECPKYVKSNRLVLATGLRNSPQRETRGLFGAIAGFIEGGWQGMVDGWYGYHHSNEQGS
GYAADKESTQKAIDGVTNKVNSIIDKMNTQFEAVGREFNNLERRIENLNKKMEDGFLDVW
TYNAELLVLMENERTLDFHDSNVKNLYDKVRLQLRDNAKELGNGCFEFYHKCDNECMESV
RNGTYDYPQYSEEARLKREEISS
GRLVPRGSPGSGYIPEAPRDGQAYVRKDGEWVLLSTFLTGHHHHHH*

FIG. 4 (Cont'd)

>xHA.4b(SEQ ID NO:7)
Met Lys Leu Cys Ile Leu Leu Ala Val Val Ala Phe Val Gly Leu Ser Leu Gly
RSDQICIGYHANNSTEQVDTIMEKNVTVTHAQDILEKKHNGKLCDLDGVKPLILRDCSVA
GWLLGNPMCDEFINVPEWSYIVEKANPVNDLCYPGDFNDYEELKHLL
*SRINHFEKIQIIPKSSWSSHEASLGVSSACLYTGTSSFFRNVVWLITKNSTYPTIKTSYN*
*NTNQEDLLVLWGIHHPNDAAEQTTLYQNPTTYISVGT*
STLNQRLVPRIATRSKVNGQSGRMEFFWTILKPNDA
INFESNGNFIAPEYAYKIVKKGDSTIMKSELEYGNCNTKCQTPMGAINSSMPFHNIHPLT
IGECPKYVKSNRLVLATGLRNSPQRETRGLFGAIAGFIEGGWQGMVDGWYGYHHSNEQGS
GYAADKESTQKAIDGVTNKVNSIIDKMNTQFEAVGREFNNLERRIENLNKKMEDGFLDVW
TYNAELLVLMENERTLDFHDSNVKNLYDKVRLQLRDNAKELGNGCFEFYHKCDNECMESV
RNGTYDYPQYSEEARLKREEISS
GRLVPRGSPGSGYIPEAPRDGQAYVRKDGEWVLLSTFLTGHHHHH*

>xHA.4c(SEQ ID NO:8)
Met Lys Leu Cys Ile Leu Leu Ala Val Val Ala Phe Val Gly Leu Ser Leu Gly
RSDQICIGYHANNSTEQVDTIMEKNVTVTHAQDILEKKHNGKLCDLDGVKPLILRDCSVA
GWLLGNPMCDEFINVPEWSYIVEKANPVNDLCYPGDFNDYEELKHLL
*SRINHFEKIQIIPKSSWSSHEASLGVSSACLYAGASSFFRNVVWLIAKNSTYPTIKASYN*
*NTNQEDLLVLWGIHHPNDAAEQTALYQNPTTYISVGT*
STLNQRLVPRIATRSKVNGQSGRMEFFWTILKPNDA
INFESNGNFIAPEYAYKIVKKGDSTIMKSELEYGNCNTKCQTPMGAINSSMPFHNIHPLT
IGECPKYVKSNRLVLATGLRNSPQRETRGLFGAIAGFIEGGWQGMVDGWYGYHHSNEQGS
GYAADKESTQKAIDGVTNKVNSIIDKMNTQFEAVGREFNNLERRIENLNKKMEDGFLDVW
TYNAELLVLMENERTLDFHDSNVKNLYDKVRLQLRDNAKELGNGCFEFYHKCDNECMESV
RNGTYDYPQYSEEARLKREEISS
GRLVPRGSPGSGYIPEAPRDGQAYVRKDGEWVLLSTFLTGHHHHH*

>xHA.5a(SEQ ID NO:9)
Met Lys Leu Cys Ile Leu Leu Ala Val Val Ala Phe Val Gly Leu Ser Leu Gly
RSDQICIGYHANNSTEQVDTIMEKNVTVTHAQDILEKKHNGKLCDLDGVKPLILRDCSVA
GWLLGNPMCDEFINVPEWSYIVEKANPVNDLCYPGDFNDYEELKHLL
*SRINHFEKIQIIPKSAWSAHTASLGVSSACLYTGTASFFRNVVWLITKNSAYPTIKTSYN*
*NTNQEDLLVLWGIHHPNDAAEQTTLYQNPTTYISVGT*
STLNQRLVPRIATRSKVNGQSGRMEFFWTILKPNDA
INFESNGNFIAPEYAYKIVKKGDSTIMKSELEYGNCNTKCQTPMGAINSSMPFHNIHPLT
IGECPKYVKSNRLVLATGLRNSPQRETRGLFGAIAGFIEGGWQGMVDGWYGYHHSNEQGS
GYAADKESTQKAIDGVTNKVNSIIDKMNTQFEAVGREFNNLERRIENLNKKMEDGFLDVW
TYNAELLVLMENERTLDFHDSNVKNLYDKVRLQLRDNAKELGNGCFEFYHKCDNECMESV
RNGTYDYPQYSEEARLKREEISS
GRLVPRGSPGSGYIPEAPRDGQAYVRKDGEWVLLSTFLTGHHHHH*

FIG. 4 (Cont'd)

\>xHA.5b(SEQ ID NO:10)
Met Lys Leu Cys Ile Leu Leu Ala Val Val Ala Phe Val Gly Leu Ser Leu Gly
RSDQICIGYHANNSTEQVDTIMEKNVTVTHAQDILEKKHNGKLCDLDGVKPLILRDCSVA
GWLLGNPMCDEFINVPEWSYIVEKANPVNDLCYPGDFNDYEELKHLL
*SRINHFEKIQIIPKSAWSAHTASLGVSSACLYTGAASFFRNVVWLIAKNSAYPTIKASYN*
*NTNQEDLLVLWGIHHPNDAAEQTALYQNPTTYISVGT*
STLNQRLVPRIATRSKVNGQSGRMEFFWTILKPNDA
INFESNGNFIAPEYAYKIVKKGDSTIMKSELEYGNCNTKCQTPMGAINSSMPFHNIHPLT
IGECPKYVKSNRLVLATGLRNSPQRETRGLFGAIAGFIEGGWQGMVDGWYGYHHSNEQGS
GYAADKESTQKAIDGVTNKVNSIIDKMNTQFEAVGREFNNLERRIENLNKKMEDGFLDVW
TYNAELLVLMENERTLDFHDSNVKNLYDKVRLQLRDNAKELGNGCFEFYHKCDNECMESV
RNGTYDYPQYSEEARLKREEISS
GRLVPRGSPGSGYIPEAPRDGQAYVRKDGEWVLLSTFLTGHHHHHH\*

FIG. 4 (Cont'd)

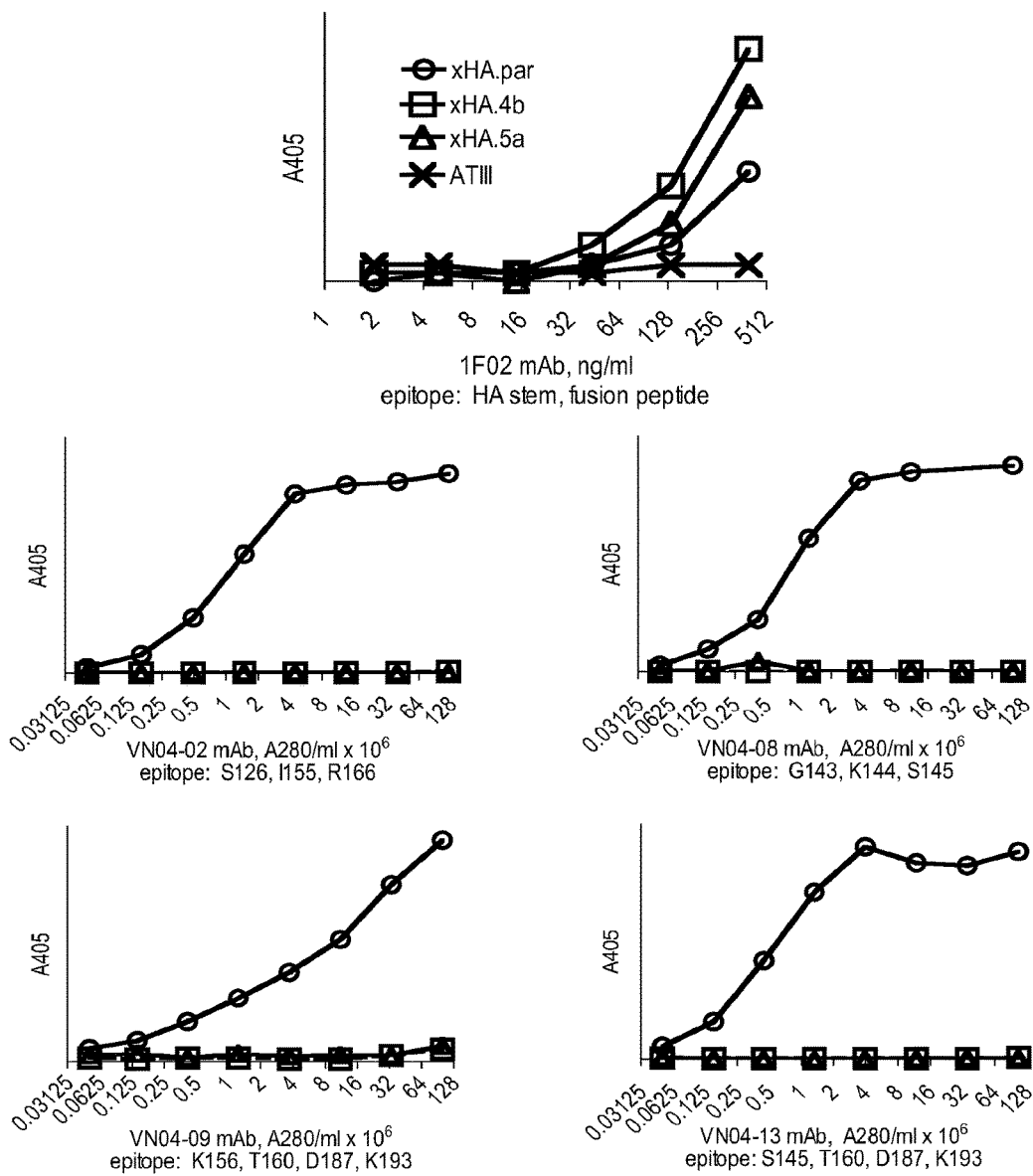

FIGURE 6
A.
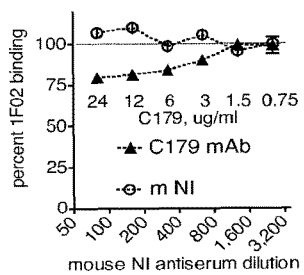
B.
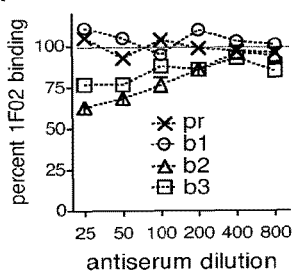 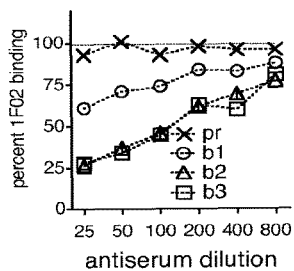
C.
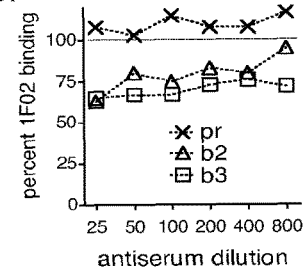 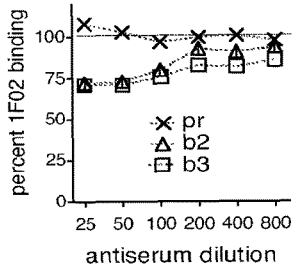
D.
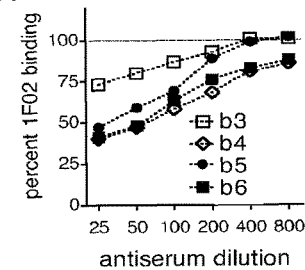 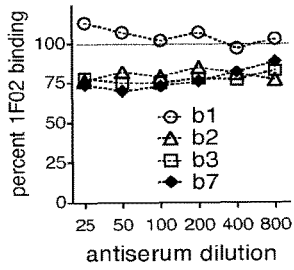 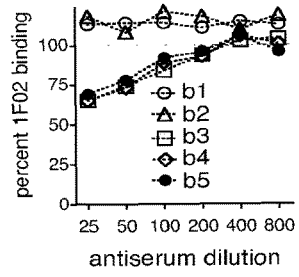

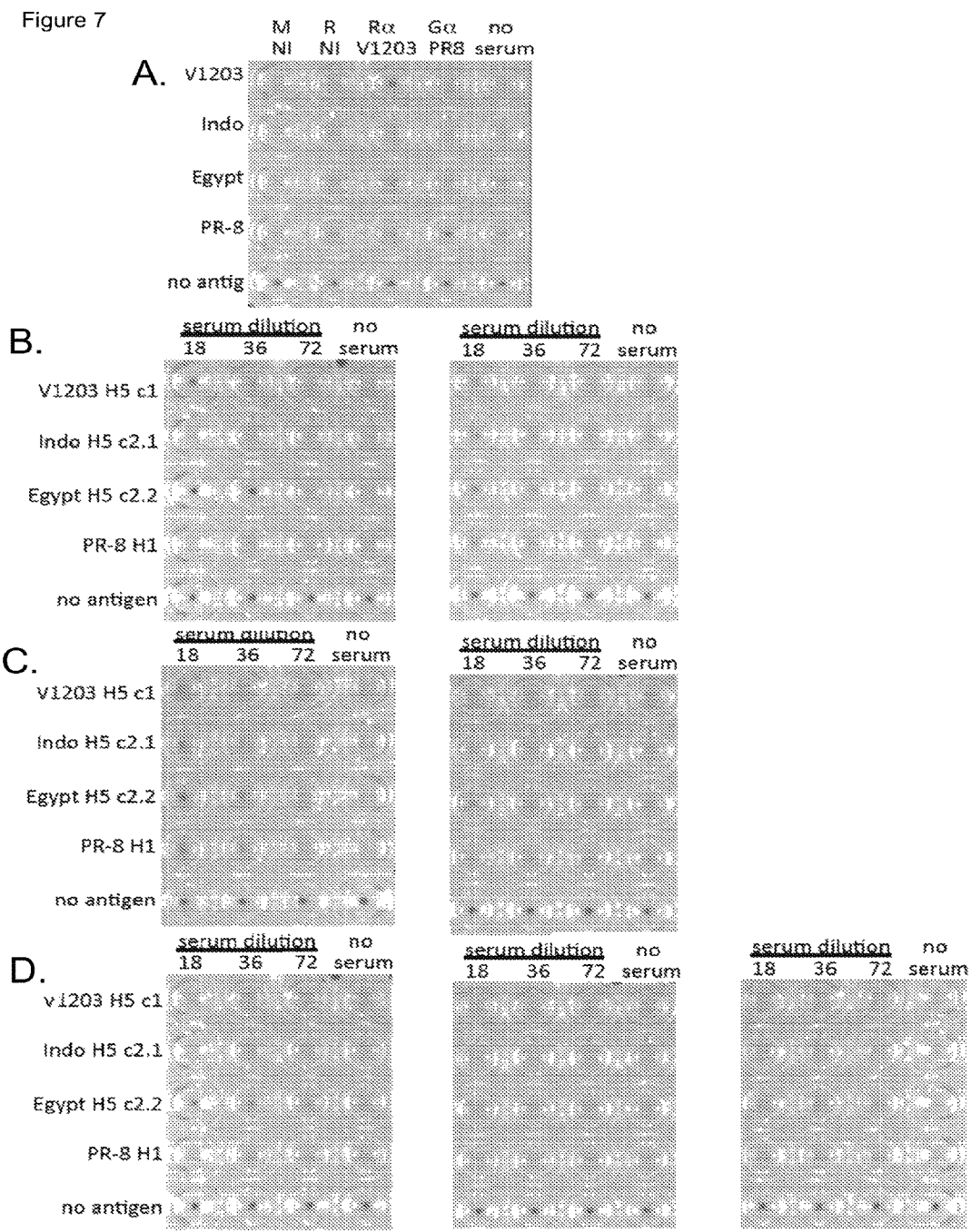

SEQUENCE LISTING

```
<160> NUMBER OF SEQ ID NOS: 15

<210> SEQ ID NO 1
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Lys Leu Cys Ile Leu Leu Ala Val Val Ala Phe Val Gly Leu Ser
1               5                   10                  15

Leu Gly Arg Ser Asp Gln Ile Cys Ile Gly Tyr His Ala Asn Asn Ser
            20                  25                  30

Thr Glu Gln Val Asp Thr Ile Met Glu Lys Asn Val Thr Val Thr His
        35                  40                  45

Ala Gln Asp Ile Leu Glu Lys Lys His Asn Gly Lys Leu Cys Asp Leu
    50                  55                  60
```

```
Asp Gly Val Lys Pro Leu Ile Leu Arg Asp Cys Ser Val Ala Gly Trp
 65                  70                  75                  80

Leu Leu Gly Asn Pro Met Cys Asp Glu Phe Ile Asn Val Pro Glu Trp
                 85                  90                  95

Ser Tyr Ile Val Glu Lys Ala Asn Pro Val Asn Asp Leu Cys Tyr Pro
            100                 105                 110

Gly Asp Phe Asn Asp Tyr Glu Glu Leu Lys His Leu Leu Ser Arg Ile
        115                 120                 125

Asn His Phe Glu Lys Ile Gln Ile Ile Pro Lys Ser Trp Ser Ser
    130                 135                 140

His Glu Ala Ser Leu Gly Val Ser Ser Ala Cys Pro Tyr Gln Gly Lys
145                 150                 155                 160

Ser Ser Phe Phe Arg Asn Val Val Trp Leu Ile Lys Lys Asn Ser Thr
                165                 170                 175

Tyr Pro Thr Ile Lys Arg Ser Tyr Asn Asn Thr Asn Gln Glu Asp Leu
            180                 185                 190

Leu Val Leu Trp Gly Ile His His Pro Asn Asp Ala Ala Glu Gln Thr
        195                 200                 205

Lys Leu Tyr Gln Asn Pro Thr Thr Tyr Ile Ser Val Gly Thr Ser Thr
210                 215                 220

Leu Asn Gln Arg Leu Val Pro Arg Ile Ala Thr Arg Ser Lys Val Asn
225                 230                 235                 240

Gly Gln Ser Gly Arg Met Glu Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270

Ala Tyr Lys Ile Val Lys Lys Gly Asp Ser Thr Ile Met Lys Ser Glu
        275                 280                 285

Leu Glu Tyr Gly Asn Cys Asn Thr Lys Cys Gln Thr Pro Met Gly Ala
290                 295                 300

Ile Asn Ser Ser Met Pro Phe His Asn Ile His Pro Leu Thr Ile Gly
305                 310                 315                 320

Glu Cys Pro Lys Tyr Val Lys Ser Asn Arg Leu Val Leu Ala Thr Gly
                325                 330                 335

Leu Arg Asn Ser Pro Gln Arg Glu Thr Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480
```

```
Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Ser Gly Arg Leu Val Pro Arg Gly
        515                 520                 525

Ser Pro Gly Ser Gly Tyr Ile Pro Glu Ala Pro Arg Asp Gly Gln Ala
    530                 535                 540

Tyr Val Arg Lys Asp Gly Glu Trp Val Leu Leu Ser Thr Phe Leu Thr
545                 550                 555                 560

Gly His His His His His His
                565
```

<210> SEQ ID NO 2
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Lys Leu Cys Ile Leu Leu Ala Val Val Ala Phe Val Gly Leu Ser
1               5                   10                  15

Leu Gly Arg Ser Asp Gln Ile Cys Ile Gly Tyr His Ala Asn Asn Ser
            20                  25                  30

Thr Glu Gln Val Asp Thr Ile Met Glu Lys Asn Val Thr Val Thr His
        35                  40                  45

Ala Gln Asp Ile Leu Glu Lys Lys His Asn Gly Lys Leu Cys Asp Leu
    50                  55                  60

Asp Gly Val Lys Pro Leu Ile Leu Arg Asp Cys Ser Val Ala Gly Trp
65                  70                  75                  80

Leu Leu Gly Asn Pro Met Cys Asp Glu Phe Ile Asn Val Pro Glu Trp
                85                  90                  95

Ser Tyr Ile Val Glu Lys Ala Asn Pro Val Asn Asp Leu Cys Tyr Pro
            100                 105                 110

Gly Asp Phe Asn Asp Tyr Glu Glu Leu Lys His Leu Leu Ser Arg Ile
        115                 120                 125

Asn His Phe Glu Lys Ile Gln Ile Ile Pro Lys Ser Tyr Trp Ser Asp
    130                 135                 140

His Asn Ala Ser Leu Gly Val Ser Ser Ala Cys Leu Tyr Lys Glu Glu
145                 150                 155                 160

Phe Ser Phe Phe Arg Asn Val Val Trp Leu Thr Glu Lys Asn Ser Ala
                165                 170                 175

Tyr Pro Thr Ile Lys Gly Ser Tyr Asn Asn Thr Asn Gln Glu Asp Leu
            180                 185                 190

Leu Val Leu Trp Gly Ile His His Pro Asn Asp Ala Ala Glu Gln Thr
        195                 200                 205

Glu Leu Tyr Gln Asn Pro Thr Thr Tyr Ile Ser Val Gly Thr Ser Thr
    210                 215                 220

Leu Asn Gln Arg Leu Val Pro Arg Ile Ala Thr Arg Ser Lys Val Asn
225                 230                 235                 240

Gly Gln Ser Gly Arg Met Glu Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270
```

```
Ala Tyr Lys Ile Val Lys Lys Gly Asp Ser Thr Ile Met Lys Ser Glu
            275                 280                 285

Leu Glu Tyr Gly Asn Cys Asn Thr Lys Cys Gln Thr Pro Met Gly Ala
        290                 295                 300

Ile Asn Ser Ser Met Pro Phe His Asn Ile His Pro Leu Thr Ile Gly
305                 310                 315                 320

Glu Cys Pro Lys Tyr Val Lys Ser Asn Arg Leu Val Leu Ala Thr Gly
                325                 330                 335

Leu Arg Asn Ser Pro Gln Arg Glu Thr Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Ser Gly Arg Leu Val Pro Arg Gly
        515                 520                 525

Ser Pro Gly Ser Gly Tyr Ile Pro Glu Ala Pro Arg Asp Gly Gln Ala
    530                 535                 540

Tyr Val Arg Lys Asp Gly Glu Trp Val Leu Leu Ser Thr Phe Leu Thr
545                 550                 555                 560

Gly His His His His His
            565

<210> SEQ ID NO 3
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Lys Leu Cys Ile Leu Leu Ala Val Val Ala Phe Val Gly Leu Ser
1               5                   10                  15

Leu Gly Arg Ser Asp Gln Ile Cys Ile Gly Tyr His Ala Asn Asn Ser
            20                  25                  30

Thr Glu Gln Val Asp Thr Ile Met Glu Lys Asn Val Thr Val Thr His
        35                  40                  45

Ala Gln Asp Ile Leu Glu Lys Lys His Asn Gly Lys Leu Cys Asp Leu
    50                  55                  60
```

```
Asp Gly Val Lys Pro Leu Ile Leu Arg Asp Cys Ser Val Ala Gly Trp
 65                  70                  75                  80

Leu Leu Gly Asn Pro Met Cys Asp Glu Phe Ile Asn Val Pro Glu Trp
                 85                  90                  95

Ser Tyr Ile Val Glu Lys Ala Asn Pro Val Asn Asp Leu Cys Tyr Pro
            100                 105                 110

Gly Asp Phe Asn Asp Tyr Glu Glu Leu Lys His Leu Leu Ser Arg Ile
        115                 120                 125

Asn His Phe Glu Lys Ile Gln Ile Ile Pro Lys Ser Ser Trp Ser Ser
    130                 135                 140

His Glu Ala Ser Leu Gly Val Ser Ser Ala Cys Pro Tyr Gln Gly Thr
145                 150                 155                 160

Ala Ser Phe Phe Arg Asn Val Val Trp Leu Ile Lys Lys Asn Ser Thr
                165                 170                 175

Tyr Pro Thr Ile Lys Arg Ser Tyr Asn Asn Thr Asn Gln Glu Asp Leu
            180                 185                 190

Leu Val Leu Trp Gly Ile His His Pro Asn Asp Ala Ala Glu Gln Thr
        195                 200                 205

Lys Leu Tyr Gln Asn Pro Thr Thr Tyr Ile Ser Val Gly Thr Ser Thr
    210                 215                 220

Leu Asn Gln Arg Leu Val Pro Arg Ile Ala Thr Arg Ser Lys Val Asn
225                 230                 235                 240

Gly Gln Ser Gly Arg Met Glu Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270

Ala Tyr Lys Ile Val Lys Lys Gly Asp Ser Thr Ile Met Lys Ser Glu
        275                 280                 285

Leu Glu Tyr Gly Asn Cys Asn Thr Lys Cys Gln Thr Pro Met Gly Ala
    290                 295                 300

Ile Asn Ser Ser Met Pro Phe His Asn Ile His Pro Leu Thr Ile Gly
305                 310                 315                 320

Glu Cys Pro Lys Tyr Val Lys Ser Asn Arg Leu Val Leu Ala Thr Gly
                325                 330                 335

Leu Arg Asn Ser Pro Gln Arg Glu Thr Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480
```

```
Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Ser Gly Arg Leu Val Pro Arg Gly
            515                 520                 525

Ser Pro Gly Ser Gly Tyr Ile Pro Glu Ala Pro Arg Asp Gly Gln Ala
            530                 535                 540

Tyr Val Arg Lys Asp Gly Glu Trp Val Leu Leu Ser Thr Phe Leu Thr
545                 550                 555                 560

Gly His His His His His His
                565
```

<210> SEQ ID NO 4
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Lys Leu Cys Ile Leu Leu Ala Val Val Ala Phe Val Gly Leu Ser
1               5                   10                  15

Leu Gly Arg Ser Asp Gln Ile Cys Ile Gly Tyr His Ala Asn Asn Ser
            20                  25                  30

Thr Glu Gln Val Asp Thr Ile Met Glu Lys Asn Val Thr Val Thr His
        35                  40                  45

Ala Gln Asp Ile Leu Glu Lys Lys His Asn Gly Lys Leu Cys Asp Leu
    50                  55                  60

Asp Gly Val Lys Pro Leu Ile Leu Arg Asp Cys Ser Val Ala Gly Trp
65                  70                  75                  80

Leu Leu Gly Asn Pro Met Cys Asp Glu Phe Ile Asn Val Pro Glu Trp
                85                  90                  95

Ser Tyr Ile Val Glu Lys Ala Asn Pro Val Asn Asp Leu Cys Tyr Pro
            100                 105                 110

Gly Asp Phe Asn Asp Tyr Glu Glu Leu Lys His Leu Leu Ser Arg Ile
        115                 120                 125

Asn His Phe Glu Lys Ile Gln Ile Ile Pro Lys Ser Ala Trp Ser Ser
    130                 135                 140

His Glu Ala Ser Leu Gly Val Ser Ser Ala Cys Pro Tyr Gln Gly Lys
145                 150                 155                 160

Ser Ser Phe Phe Arg Asn Val Val Trp Leu Ile Lys Lys Asn Ser Thr
                165                 170                 175

Tyr Pro Thr Ile Lys Thr Ser Tyr Asn Asn Thr Asn Gln Glu Asp Leu
            180                 185                 190

Leu Val Leu Trp Gly Ile His His Pro Asn Asp Ala Ala Glu Gln Thr
        195                 200                 205

Lys Leu Tyr Gln Asn Pro Thr Thr Tyr Ile Ser Val Gly Thr Ser Thr
    210                 215                 220

Leu Asn Gln Arg Leu Val Pro Arg Ile Ala Thr Arg Ser Lys Val Asn
225                 230                 235                 240

Gly Gln Ser Gly Arg Met Glu Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270
```

Ala Tyr Lys Ile Val Lys Lys Gly Asp Ser Thr Ile Met Lys Ser Glu
            275                 280                 285

Leu Glu Tyr Gly Asn Cys Asn Thr Lys Cys Gln Thr Pro Met Gly Ala
        290                 295                 300

Ile Asn Ser Ser Met Pro Phe His Asn Ile His Pro Leu Thr Ile Gly
305                 310                 315                 320

Glu Cys Pro Lys Tyr Val Lys Ser Asn Arg Leu Val Leu Ala Thr Gly
                325                 330                 335

Leu Arg Asn Ser Pro Gln Arg Glu Thr Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Ser Gly Arg Leu Val Pro Arg Gly
        515                 520                 525

Ser Pro Gly Ser Gly Tyr Ile Pro Glu Ala Pro Arg Asp Gly Gln Ala
530                 535                 540

Tyr Val Arg Lys Asp Gly Glu Trp Val Leu Leu Ser Thr Phe Leu Thr
545                 550                 555                 560

Gly His His His His His
            565

<210> SEQ ID NO 5
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Lys Leu Cys Ile Leu Leu Ala Val Val Ala Phe Val Gly Leu Ser
1               5                   10                  15

Leu Gly Arg Ser Asp Gln Ile Cys Ile Gly Tyr His Ala Asn Asn Ser
            20                  25                  30

Thr Glu Gln Val Asp Thr Ile Met Glu Lys Asn Val Thr Val Thr His
        35                  40                  45

Ala Gln Asp Ile Leu Glu Lys Lys His Asn Gly Lys Leu Cys Asp Leu
    50                  55                  60

```
Asp Gly Val Lys Pro Leu Ile Leu Arg Asp Cys Ser Val Ala Gly Trp
 65                  70                  75                  80

Leu Leu Gly Asn Pro Met Cys Asp Glu Phe Ile Asn Val Pro Glu Trp
                 85                  90                  95

Ser Tyr Ile Val Glu Lys Ala Asn Pro Val Asn Asp Leu Cys Tyr Pro
            100                 105                 110

Gly Asp Phe Asn Asp Tyr Glu Glu Leu Lys His Leu Leu Ser Arg Ile
        115                 120                 125

Asn His Phe Glu Lys Ile Gln Ile Ile Pro Lys Ser Ser Trp Ser Ser
    130                 135                 140

His Glu Ala Ser Leu Gly Val Ser Ser Ala Cys Pro Tyr Gln Gly Lys
145                 150                 155                 160

Ser Ser Phe Phe Arg Asn Val Val Trp Leu Ile Ala Lys Asn Ser Thr
                165                 170                 175

Tyr Pro Thr Ile Lys Arg Ser Tyr Asn Asn Thr Asn Gln Glu Asp Leu
            180                 185                 190

Leu Val Leu Trp Gly Ile His His Pro Asn Asp Ala Ala Glu Gln Thr
        195                 200                 205

Lys Leu Tyr Gln Asn Pro Thr Thr Tyr Ile Ser Val Gly Thr Ser Thr
    210                 215                 220

Leu Asn Gln Arg Leu Val Pro Arg Ile Ala Thr Arg Ser Lys Val Asn
225                 230                 235                 240

Gly Gln Ser Gly Arg Met Glu Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270

Ala Tyr Lys Ile Val Lys Lys Gly Asp Ser Thr Ile Met Lys Ser Glu
        275                 280                 285

Leu Glu Tyr Gly Asn Cys Asn Thr Lys Cys Gln Thr Pro Met Gly Ala
    290                 295                 300

Ile Asn Ser Ser Met Pro Phe His Asn Ile His Pro Leu Thr Ile Gly
305                 310                 315                 320

Glu Cys Pro Lys Tyr Val Lys Ser Asn Arg Leu Val Leu Ala Thr Gly
                325                 330                 335

Leu Arg Asn Ser Pro Gln Arg Glu Thr Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480
```

```
Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Ser Gly Arg Leu Val Pro Arg Gly
        515                 520                 525

Ser Pro Gly Ser Gly Tyr Ile Pro Glu Ala Pro Arg Asp Gly Gln Ala
    530                 535                 540

Tyr Val Arg Lys Asp Gly Glu Trp Val Leu Leu Ser Thr Phe Leu Thr
545                 550                 555                 560

Gly His His His His His
                565
```

<210> SEQ ID NO 6
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Lys Leu Cys Ile Leu Leu Ala Val Val Ala Phe Val Gly Leu Ser
1               5                   10                  15

Leu Gly Arg Ser Asp Gln Ile Cys Ile Gly Tyr His Ala Asn Asn Ser
            20                  25                  30

Thr Glu Gln Val Asp Thr Ile Met Glu Lys Asn Val Thr Val Thr His
        35                  40                  45

Ala Gln Asp Ile Leu Glu Lys Lys His Asn Gly Lys Leu Cys Asp Leu
    50                  55                  60

Asp Gly Val Lys Pro Leu Ile Leu Arg Asp Cys Ser Val Ala Gly Trp
65                  70                  75                  80

Leu Leu Gly Asn Pro Met Cys Asp Glu Phe Ile Asn Val Pro Glu Trp
                85                  90                  95

Ser Tyr Ile Val Glu Lys Ala Asn Pro Val Asn Asp Leu Cys Tyr Pro
            100                 105                 110

Gly Asp Phe Asn Asp Tyr Glu Glu Leu Lys His Leu Leu Ser Arg Ile
        115                 120                 125

Asn His Phe Glu Lys Ile Gln Ile Ile Pro Lys Ser Ser Trp Ser Ser
    130                 135                 140

His Glu Ala Ser Leu Gly Val Ser Ser Ala Cys Leu Tyr Lys Gly Glu
145                 150                 155                 160

Ser Ser Phe Phe Arg Asn Val Val Trp Leu Ile Glu Lys Asn Ser Thr
                165                 170                 175

Tyr Pro Thr Ile Lys Gly Ser Tyr Asn Asn Thr Asn Gln Glu Asp Leu
            180                 185                 190

Leu Val Leu Trp Gly Ile His His Pro Asn Asp Ala Ala Glu Gln Thr
        195                 200                 205

Glu Leu Tyr Gln Asn Pro Thr Thr Tyr Ile Ser Val Gly Thr Ser Thr
    210                 215                 220

Leu Asn Gln Arg Leu Val Pro Arg Ile Ala Thr Arg Ser Lys Val Asn
225                 230                 235                 240

Gly Gln Ser Gly Arg Met Glu Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270
```

```
Ala Tyr Lys Ile Val Lys Lys Gly Asp Ser Thr Ile Met Lys Ser Glu
            275                 280                 285

Leu Glu Tyr Gly Asn Cys Asn Thr Lys Cys Gln Thr Pro Met Gly Ala
        290                 295                 300

Ile Asn Ser Ser Met Pro Phe His Asn Ile His Pro Leu Thr Ile Gly
305                 310                 315                 320

Glu Cys Pro Lys Tyr Val Lys Ser Asn Arg Leu Val Leu Ala Thr Gly
                325                 330                 335

Leu Arg Asn Ser Pro Gln Arg Glu Thr Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Ser Gly Arg Leu Val Pro Arg Gly
        515                 520                 525

Ser Pro Gly Ser Gly Tyr Ile Pro Glu Ala Pro Arg Asp Gly Gln Ala
530                 535                 540

Tyr Val Arg Lys Asp Gly Glu Trp Val Leu Leu Ser Thr Phe Leu Thr
545                 550                 555                 560

Gly His His His His His
            565

<210> SEQ ID NO 7
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Lys Leu Cys Ile Leu Leu Ala Val Val Ala Phe Val Gly Leu Ser
1               5                   10                  15

Leu Gly Arg Ser Asp Gln Ile Cys Ile Gly Tyr His Ala Asn Asn Ser
            20                  25                  30

Thr Glu Gln Val Asp Thr Ile Met Glu Lys Asn Val Thr Val Thr His
        35                  40                  45

Ala Gln Asp Ile Leu Glu Lys Lys His Asn Gly Lys Leu Cys Asp Leu
    50                  55                  60
```

```
Asp Gly Val Lys Pro Leu Ile Leu Arg Asp Cys Ser Val Ala Gly Trp
 65                  70                  75                  80

Leu Leu Gly Asn Pro Met Cys Asp Glu Phe Ile Asn Val Pro Glu Trp
                 85                  90                  95

Ser Tyr Ile Val Glu Lys Ala Asn Pro Val Asn Asp Leu Cys Tyr Pro
            100                 105                 110

Gly Asp Phe Asn Asp Tyr Glu Glu Leu Lys His Leu Leu Ser Arg Ile
        115                 120                 125

Asn His Phe Glu Lys Ile Gln Ile Ile Pro Lys Ser Ser Trp Ser Ser
    130                 135                 140

His Glu Ala Ser Leu Gly Val Ser Ser Ala Cys Leu Tyr Thr Gly Thr
145                 150                 155                 160

Ser Ser Phe Phe Arg Asn Val Val Trp Leu Ile Thr Lys Asn Ser Thr
                165                 170                 175

Tyr Pro Thr Ile Lys Thr Ser Tyr Asn Asn Thr Asn Gln Glu Asp Leu
            180                 185                 190

Leu Val Leu Trp Gly Ile His His Pro Asn Asp Ala Ala Glu Gln Thr
        195                 200                 205

Thr Leu Tyr Gln Asn Pro Thr Thr Tyr Ile Ser Val Gly Thr Ser Thr
    210                 215                 220

Leu Asn Gln Arg Leu Val Pro Arg Ile Ala Thr Arg Ser Lys Val Asn
225                 230                 235                 240

Gly Gln Ser Gly Arg Met Glu Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270

Ala Tyr Lys Ile Val Lys Lys Gly Asp Ser Thr Ile Met Lys Ser Glu
        275                 280                 285

Leu Glu Tyr Gly Asn Cys Asn Thr Lys Cys Gln Thr Pro Met Gly Ala
    290                 295                 300

Ile Asn Ser Ser Met Pro Phe His Asn Ile His Pro Leu Thr Ile Gly
305                 310                 315                 320

Glu Cys Pro Lys Tyr Val Lys Ser Asn Arg Leu Val Leu Ala Thr Gly
                325                 330                 335

Leu Arg Asn Ser Pro Gln Arg Glu Thr Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480
```

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Ser Gly Arg Leu Val Pro Arg Gly
            515                 520                 525

Ser Pro Gly Ser Gly Tyr Ile Pro Glu Ala Pro Arg Asp Gly Gln Ala
            530                 535                 540

Tyr Val Arg Lys Asp Gly Glu Trp Val Leu Leu Ser Thr Phe Leu Thr
545                 550                 555                 560

Gly His His His His His His
                565

<210> SEQ ID NO 8
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Lys Leu Cys Ile Leu Leu Ala Val Val Ala Phe Val Gly Leu Ser
1               5                   10                  15

Leu Gly Arg Ser Asp Gln Ile Cys Ile Gly Tyr His Ala Asn Asn Ser
            20                  25                  30

Thr Glu Gln Val Asp Thr Ile Met Glu Lys Asn Val Thr Val Thr His
        35                  40                  45

Ala Gln Asp Ile Leu Glu Lys Lys His Asn Gly Lys Leu Cys Asp Leu
    50                  55                  60

Asp Gly Val Lys Pro Leu Ile Leu Arg Asp Cys Ser Val Ala Gly Trp
65                  70                  75                  80

Leu Leu Gly Asn Pro Met Cys Asp Glu Phe Ile Asn Val Pro Glu Trp
                85                  90                  95

Ser Tyr Ile Val Glu Lys Ala Asn Pro Val Asn Asp Leu Cys Tyr Pro
            100                 105                 110

Gly Asp Phe Asn Asp Tyr Glu Glu Leu Lys His Leu Leu Ser Arg Ile
        115                 120                 125

Asn His Phe Glu Lys Ile Gln Ile Ile Pro Lys Ser Ser Trp Ser Ser
    130                 135                 140

His Glu Ala Ser Leu Gly Val Ser Ser Ala Cys Leu Tyr Ala Gly Ala
145                 150                 155                 160

Ser Ser Phe Phe Arg Asn Val Val Trp Leu Ile Ala Lys Asn Ser Thr
                165                 170                 175

Tyr Pro Thr Ile Lys Ala Ser Tyr Asn Asn Thr Asn Gln Glu Asp Leu
            180                 185                 190

Leu Val Leu Trp Gly Ile His His Pro Asn Asp Ala Ala Glu Gln Thr
        195                 200                 205

Ala Leu Tyr Gln Asn Pro Thr Thr Tyr Ile Ser Val Gly Thr Ser Thr
    210                 215                 220

Leu Asn Gln Arg Leu Val Pro Arg Ile Ala Thr Arg Ser Lys Val Asn
225                 230                 235                 240

Gly Gln Ser Gly Arg Met Glu Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270

```
Ala Tyr Lys Ile Val Lys Lys Gly Asp Ser Thr Ile Met Lys Ser Glu
            275                 280                 285

Leu Glu Tyr Gly Asn Cys Asn Thr Lys Cys Gln Thr Pro Met Gly Ala
        290                 295                 300

Ile Asn Ser Ser Met Pro Phe His Asn Ile His Pro Leu Thr Ile Gly
305                 310                 315                 320

Glu Cys Pro Lys Tyr Val Lys Ser Asn Arg Leu Val Leu Ala Thr Gly
                325                 330                 335

Leu Arg Asn Ser Pro Gln Arg Glu Thr Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Ser Gly Arg Leu Val Pro Arg Gly
        515                 520                 525

Ser Pro Gly Ser Gly Tyr Ile Pro Glu Ala Pro Arg Asp Gly Gln Ala
    530                 535                 540

Tyr Val Arg Lys Asp Gly Glu Trp Val Leu Leu Ser Thr Phe Leu Thr
545                 550                 555                 560

Gly His His His His His His
            565

<210> SEQ ID NO 9
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Lys Leu Cys Ile Leu Leu Ala Val Val Ala Phe Val Gly Leu Ser
1               5                   10                  15

Leu Gly Arg Ser Asp Gln Ile Cys Ile Gly Tyr His Ala Asn Asn Ser
            20                  25                  30

Thr Glu Gln Val Asp Thr Ile Met Glu Lys Asn Val Thr Val Thr His
        35                  40                  45

Ala Gln Asp Ile Leu Glu Lys Lys His Asn Gly Lys Leu Cys Asp Leu
    50                  55                  60
```

```
Asp Gly Val Lys Pro Leu Ile Leu Arg Asp Cys Ser Val Ala Gly Trp
 65                  70                  75                  80

Leu Leu Gly Asn Pro Met Cys Asp Glu Phe Ile Asn Val Pro Glu Trp
                 85                  90                  95

Ser Tyr Ile Val Glu Lys Ala Asn Pro Val Asn Asp Leu Cys Tyr Pro
            100                 105                 110

Gly Asp Phe Asn Asp Tyr Glu Glu Leu Lys His Leu Leu Ser Arg Ile
        115                 120                 125

Asn His Phe Glu Lys Ile Gln Ile Ile Pro Lys Ser Ala Trp Ser Ala
    130                 135                 140

His Thr Ala Ser Leu Gly Val Ser Ser Ala Cys Leu Tyr Thr Gly Thr
145                 150                 155                 160

Ala Ser Phe Phe Arg Asn Val Val Trp Leu Ile Thr Lys Asn Ser Ala
                165                 170                 175

Tyr Pro Thr Ile Lys Thr Ser Tyr Asn Asn Thr Asn Gln Glu Asp Leu
            180                 185                 190

Leu Val Leu Trp Gly Ile His His Pro Asn Asp Ala Ala Glu Gln Thr
        195                 200                 205

Thr Leu Tyr Gln Asn Pro Thr Thr Tyr Ile Ser Val Gly Thr Ser Thr
    210                 215                 220

Leu Asn Gln Arg Leu Val Pro Arg Ile Ala Thr Arg Ser Lys Val Asn
225                 230                 235                 240

Gly Gln Ser Gly Arg Met Glu Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270

Ala Tyr Lys Ile Val Lys Lys Gly Asp Ser Thr Ile Met Lys Ser Glu
        275                 280                 285

Leu Glu Tyr Gly Asn Cys Asn Thr Lys Cys Gln Thr Pro Met Gly Ala
    290                 295                 300

Ile Asn Ser Ser Met Pro Phe His Asn Ile His Pro Leu Thr Ile Gly
305                 310                 315                 320

Glu Cys Pro Lys Tyr Val Lys Ser Asn Arg Leu Val Leu Ala Thr Gly
                325                 330                 335

Leu Arg Asn Ser Pro Gln Arg Glu Thr Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480
```

-continued

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Ser Gly Arg Leu Val Pro Arg Gly
            515                 520                 525

Ser Pro Gly Ser Gly Tyr Ile Pro Glu Ala Pro Arg Asp Gly Gln Ala
            530                 535                 540

Tyr Val Arg Lys Asp Gly Glu Trp Val Leu Leu Ser Thr Phe Leu Thr
545                 550                 555                 560

Gly His His His His His His
            565

<210> SEQ ID NO 10
<211> LENGTH: 567
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Lys Leu Cys Ile Leu Leu Ala Val Val Ala Phe Val Gly Leu Ser
1               5                   10                  15

Leu Gly Arg Ser Asp Gln Ile Cys Ile Gly Tyr His Ala Asn Asn Ser
            20                  25                  30

Thr Glu Gln Val Asp Thr Ile Met Glu Lys Asn Val Thr Val Thr His
            35                  40                  45

Ala Gln Asp Ile Leu Glu Lys Lys His Asn Gly Lys Leu Cys Asp Leu
    50                  55                  60

Asp Gly Val Lys Pro Leu Ile Leu Arg Asp Cys Ser Val Ala Gly Trp
65                  70                  75                  80

Leu Leu Gly Asn Pro Met Cys Asp Glu Phe Ile Asn Val Pro Glu Trp
                85                  90                  95

Ser Tyr Ile Val Glu Lys Ala Asn Pro Val Asn Asp Leu Cys Tyr Pro
            100                 105                 110

Gly Asp Phe Asn Asp Tyr Glu Glu Leu Lys His Leu Leu Ser Arg Ile
            115                 120                 125

Asn His Phe Glu Lys Ile Gln Ile Ile Pro Lys Ser Ala Trp Ser Ala
        130                 135                 140

His Thr Ala Ser Leu Gly Val Ser Ser Ala Cys Leu Tyr Thr Gly Ala
145                 150                 155                 160

Ala Ser Phe Phe Arg Asn Val Val Trp Leu Ile Ala Lys Asn Ser Ala
                165                 170                 175

Tyr Pro Thr Ile Lys Ala Ser Tyr Asn Asn Thr Asn Gln Glu Asp Leu
            180                 185                 190

Leu Val Leu Trp Gly Ile His His Pro Asn Asp Ala Ala Glu Gln Thr
            195                 200                 205

Ala Leu Tyr Gln Asn Pro Thr Thr Tyr Ile Ser Val Gly Thr Ser Thr
        210                 215                 220

Leu Asn Gln Arg Leu Val Pro Arg Ile Ala Thr Arg Ser Lys Val Asn
225                 230                 235                 240

Gly Gln Ser Gly Arg Met Glu Phe Phe Trp Thr Ile Leu Lys Pro Asn
                245                 250                 255

Asp Ala Ile Asn Phe Glu Ser Asn Gly Asn Phe Ile Ala Pro Glu Tyr
            260                 265                 270

```
Ala Tyr Lys Ile Val Lys Lys Gly Asp Ser Thr Ile Met Lys Ser Glu
            275                 280                 285

Leu Glu Tyr Gly Asn Cys Asn Thr Lys Cys Gln Thr Pro Met Gly Ala
        290                 295                 300

Ile Asn Ser Ser Met Pro Phe His Asn Ile His Pro Leu Thr Ile Gly
305                 310                 315                 320

Glu Cys Pro Lys Tyr Val Lys Ser Asn Arg Leu Val Leu Ala Thr Gly
                325                 330                 335

Leu Arg Asn Ser Pro Gln Arg Glu Thr Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Ser Gly Arg Leu Val Pro Arg Gly
        515                 520                 525

Ser Pro Gly Ser Gly Tyr Ile Pro Glu Ala Pro Arg Asp Gly Gln Ala
    530                 535                 540

Tyr Val Arg Lys Asp Gly Glu Trp Val Leu Leu Ser Thr Phe Leu Thr
545                 550                 555                 560

Gly His His His His His
            565

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Arg Arg Lys Lys
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 12

His His His His His His
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Arg Glu Glu Ile Ser
1               5

<210> SEQ ID NO 14
<211> LENGTH: 14
<212> TYPE: PRT
<213> ORGANISM: Influenza A virus

<400> SEQUENCE: 14

Pro Gln Arg Glu Arg Arg Arg Lys Lys Arg Gly Leu Phe Gly
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Pro Gln Arg Glu Thr Arg Gly Leu Phe Gly
1               5                   10
```

VACCINE ANTIGENS THAT DIRECT IMMUNITY TO CONSERVED EPITOPES

CROSS REFERENCE TO RELATED APPLICATIONS

This application claims the benefit of U.S. patent application Ser. No. 13/993,862, filed Aug. 15, 2013, which is a national stage entry of PCT/US2011/064442, filed Dec. 12, 2011, which claims the benefit of U.S. Provisional Patent Application No. 61/457,028, filed Dec. 13, 2010, and U.S. Provisional Patent Application No. 61/626,792, filed Oct. 3, 2011, each of which is hereby incorporated by reference in its entirety.

BACKGROUND OF THE INVENTION

The present invention relates to a method of producing antigens that elicit an immune response to conserved epitopes and is therefore applicable to pathogens for which the primary immune response is directed at variable epitopes. Such a method is especially applicable to influenza vaccines. Accordingly, the invention also provides a universal vaccine against influenza.

A vaccine is designed to induce an immune response that recognizes a pathogen (or pathogen virulence factors) and thereby prevents or mitigates disease. The choice of antigens is, therefore, important. An immune response against surface exposed antigens is typically most effective against an infection. At the same time, because of this immune response, such surface exposed antigens are under constant evolutionary pressure to evolve and evade the immune system. Thus, a vaccine that elicits an immune response against a specific strain of pathogen may be extremely effective against that strain, but poorly effective against variant strains. To account for the evolution of virulent strains, the vaccine maker may therefore have to target multiple antigens, add new antigens as the pathogen evolves, or target conserved antigens.

A separate problem in vaccine design is that some epitopes elicit an undesirable immune response. For example, inducing non-neutralizing antibodies can enhance Fc-mediated infection of macrophages, which is the mechanism behind Dengue shock syndrome. Another problem is the induction of an immune response that cross reacts with host antigens. The most famous of these is Guillain-Barré syndrome which is associated with *Campylobacter* infection, but is also associated with influenza infection. Guillain-Barré syndrome was a reported side-effect of the 1976 swine flu vaccination program. Accordingly, the selection of epitopes for vaccines is far from routine.

Influenza is well known for rapidly evolving different strains, requiring new vaccines every season. Influenza A causes seasonal epidemics affecting millions every year and resulting in the death of between 250,000 and 500,000 people every year, with up to millions in some pandemic years, according to WHO. These seasonal epidemics and pandemics arise because of the constant evolution of the virus both through mutations ("antigenic drift") and through genetic reassortment that occurs when two different influenza viruses infect the same cell ("antigenic shift"). Such reassortment is greatly enhanced by the ability of influenza A to infect a variety of host species, including birds, humans, and other animals, notably pigs. Thus, recombination between two or more viruses, with different primary hosts, may result in novel and highly pathogenic strains that are responsible for the great influenza pandemics.

Among Avian H5N1 influenzas, for example, there is concern that a human-adapted H5 influenza virus will evolve by mutational (genetic drift) and/or reassortment (genetic shift) mechanisms, to cause a catastrophic pandemic. It is believed that the virus that causes the pandemic will derive from H5 influenzas that are circulating in birds today, but differ from them in ways that are impossible to predict. Therefore, not only is there interest in producing vaccines against the circulating strains of H5, there is also interest in developing vaccines that would not be restricted by inherent strain-specificity.

Such "universal vaccines" target conserved and evolutionarily stable viral epitopes, rather than the continuously changing hemagglutinin (HA) and neuraminidase (N) epitopes targeted by seasonal flu vaccines (Gerhard, W et al. *Prospects for Universal Influenza Virus Vaccine*. Emerging Infectious Diseases, 2006. 12: p. 569, Subbarao, K, et al., *Development of effective vaccines against pandemic influenza*. Immunity, 2006. 24(1): p. 5-9.). Universal flu, vaccines to date have focused on the highly conserved M2 and NP proteins (Kaiser, J., *A One-Size-Fits-All Flu Vaccine*. Science, 2006, 312:380). However, M2 and NP proteins are not abundant or easily accessible on the surface of infecting virions and the immune responses to M2 and NP do not directly prevent infection. Thus, an antibody response against M2 and NP is greatly inferior to that obtained by the standard seasonal influenza vaccine.

Haemagglutinin is abundant and surface exposed, and is a primary target of the immune response against the standard influenza vaccine. However, the HA molecule is highly variant, and the immune response to HA is overwhelmingly driven against the hypervariable regions of HA. Thus, in traditional influenza vaccination or natural infections, the protective humoral immune response is overwhelmingly directed at a limited number of continuously evolving, strain-specific, primary antigenic determinants on the surface of the influenza hemagglutinin, and there is minimal cross reaction with or protection against other serotypes of influenza. This creates a barrier to a "universal vaccine" as vaccination strategies are typically predicated on mimicking natural protective immunity.

There is now evidence of a weaker and more broadly protective type of "heterotypic" immunity, which is not based on the response to primary antigenic determinants, but instead derives from responses to conserved viral antigens. It is now thought that heterotypic influenza protection does occur at low levels in human populations.

For example, a heterosubtypic response to seasonal influenza vaccine can be observed by isolating B-cells that produce antibodies that bind to conserved epitopes (Corti, D., et al., *Heterosubtypic neutralizing antibodies are produced by individuals immunized with a seasonal influenza vaccine*. J Clin Invest, 2010. 120(5): p. 1663-1673). Natural infection can induce heterosubtypic antibodies that are cross protective, but only at very low titre (Sullivan, J. S., et al., *Heterosubtypic antiavian H5N1 influenza antibodies in intravenous immunoglobulins from globally separate populations protect against H5N1 infection in cell culture*. J Mol Genet Med, 2009. 3(2): p. 217-24; see also Sui, J., et al., Wide prevalence of heterosubtypic broadly neutralizing human antiinfluenza A antibodies. Clin Infect Dis, 2011. 52(8): p. 1003-1009; Wrammert, J., et al., *Broadly crossreactive antibodies dominate the human B cell response against 2009 pandemic H1N1 influenza virus infection*. J Exp Med, 2011. 208(1): p. 181-193). Epidemiological data collected before and during the 1957 flu pandemic suggested that heterosubtypic immunity to HA may be observed in adults but not in children (Epstein, S., Prior *H1N1 influenza infection and susceptibility of Cleveland Family Study participants during the H2N2 pandemic of 1957: an experiment of nature*. J Infect Dis., 2006. 193: p. 49-53), and raises the possibility that elicitation of protective heterotypic responses may prove effective against avian influenza viruses.

More recent studies have advanced the concept of "seasoned" immunity. Through multiple infections with different strains, a "seasoned" response to conserved epitopes may be observed. (Lynch, G. W., et al., *Seasoned adaptive antibody immunity for highly pathogenic pandemic influenza in humans*. Immunol Cell Biol, 2011, pp 1-10, Wrammert et al. J Exp Med, 2011. 208(1): p. 181-193). This response, while low, is sufficient to provide some degree of protection from heterotypic and heterosubtypic infection, and explains the greater heterosubtypic immunity observed in adults than in children. It is to be emphasized that the immunity offered by heterotypic and heterosubtypic immunity can be observed as a lower morbidity, mortality and viral shedding, but it is far inferior to the homotypic immunity usually obtained by standard vaccination or infection.

Heterotypic immunity has also been demonstrated by passive administration of a monoclonal antibody (C179) that recognizes a conserved conformational epitope on the hemagglutinin stem consisting of HA1 318-322 and HA2 47-58. C179 reduced the severity of illness and death rate in mice infected with H1, H2 or H5 influenzas (Okuno, Y., et al., *A common neutralizing epitope conserved between the hemagglutinins of influenza A virus H1 and H2 strains*. J Virol., 1993. 67: p. 2552-8; Okuno, Y., et al., *Protection against the mouse-adapted A/FM/1/47 strain of influenza A virus in mice by a monoclonal antibody with cross-neutralizing activity among H1 and H2 strains*. J Virol., 1994. 68: p. 517-20; Smirnov, Y., et al., *Prevention and treatment of bronchopneumonia in mice caused by mouse-adapted variant of avian H5N2 influenza A virus using monoclonal antibody against conserved epitope in the HA stem region*. Arch Virol., 2000. 145: p. 1733-41).

Recent attempts to create a universal vaccine have focused on eliciting an immune response against the stem/stalk domain. For example, Steel et al. (*Influenza virus vaccine based on the conserved hemagglutinin stalk domain*, mBio 1 (1): 1-9 (April 2010)) describes vaccination with a "headless" HA molecule to drive an immune response against the stalk domain of HA. Wei et al. (*Induction of broadly neutralizing HIN1 influenza antibodies by vaccination*, Science 329: 2060-2064 (27 Aug. 2010, e-pub 15 Jul. 2010)) describes how immunization with a DNA vector expressing H1N1 HA and then boosting with H1N1 seasonal vaccine or replication defective adenovirus 5 vector encoding HA stimulated the production of broadly neutralizing antibodies that recognize H1 from diverse H1 isolates, with some cross-neutralization of H3 and H5. Further analysis indicated that the immune response was directed against stem antigens. Other research in this area has also been reported. (Bommakanti et al, *Design of an HA2 based Escherichia coli expressed influenza immunogen that protects mice from pathogenic challenge*. Proc Natl Acad Sci USA, 2010. 107(31): p. 13701-6; Wang et al. *Vaccination with a synthetic peptide from the influenza virus hemagglutinin provides protection against distinct viral subtypes*. Proc Natl Acad Sci USA, 2010. 107(44): p. 18979-84.)

However, such "stem" or "headless" vaccines miss other conserved epitopes, such as those that exist on the head (Khurana, *Antigenic fingerprinting of H5N1 avian influenza using convalescent sera and monoclonal antibodies reveals potential vaccine and diagnostic targets*. PLoS Med, 2009. 6(4): p. e1000049; Krause et al., *A broadly neutralizing human monoclonal antibody that recognizes a conserved, novel epitope on the globular head of influenza H1N1 virus hemagglutinin*. J Virol, 2011. pmid_21849447; Whittle, et al., *Broadly neutralizing human antibody that recognizes the receptorbinding pocket of influenza virus hemagglutinin*. Proc Natl Acad Sci USA, 2011. 108(34): p. 1421621; Yoshida, et al., *Crossprotective potential of a novel monoclonal antibody directed against antigenic site B of the hemagglutinin of influenza A viruses*. PLoS Pathog, 2009. 5(3): p. e1000350). Antibodies to the head domain block hemagglutination, and therefore should restrict access to the receptor binding site, and therefore preventing infection via interference with viron binding to host cell sialic acid receptors.

Another site outside the stem region is the cleavage site between the HA1 and HA2 domains of HA. This region is highly conserved between influenza A and B hemagglutinin precursors, and peptide conjugate vaccines with sequences from the highly conserved maturational HA1/HA2 elicited broadly protective immune responses against lethal challenge from other A and B influenzas (Bianchi, E., et al., *Universal influenza B vaccine based on the maturational cleavage site of the hemagglutinin precursor*. J Virol., 2005. 79: p. 7380-8, 14, Horvath, A., et al., *A hemagglutinin-based multipeptide construct elicits enhanced protective immune response in mice against influenza A virus infection*. Immunol Lett., 1998. 60: p. 127-36).

Given that conserved epitopes that mediate broad neutralization are present on the HA head, as well as its stem, vaccine antigens comprised of entire trimeric hemagglutinins, rather than only the stem, or mimeitcs of selected broadly neutralizing epitopes, should offer the greatest opportunity of heterosubtypic protection.

The challenge of generating an immune response against the conserved epitopes on the head is that such conserved epitopes are structurally linked to the variable regions that are antigenically dominant. The immunodominant regions cannot be merely removed, however.

Epitopes on the surface of proteins are almost always discontinuous and conformation dependent (Barlow D J, et al., *Continuous and discontinuous protein antigenic determinants*, Nature 1986; 322:747-748). Therefore, merely deleting the immunodominant region alters the structure of the head and thus the structure of the conserved epitope. By contrast, immunization against the stem region is less problematic because the entire stem may be used.

The challenge remains to generate through vaccination an immune response against conserved antigens, that is at sufficient titre to offer meaningful protection.

SUMMARY OF THE INVENTION

The invention provides a method of reducing the immune response to an epitope while retaining protein structure, comprising: (a) identifying amino acids high on the log odds relative propensity scale (LODrps, a measure of the likelihood of an amino acid being part of an epitope) and (b) replacing at least one high LODrps amino acid with a low LODrps amino acid. By reducing or ablating the immune response to a primary/immunodominant epitope, the immune response is directed against secondary epitopes, including conserved epitopes that are weakly immunogenic.

In a related embodiment, the invention provides a method of making a vaccine that elicits an immune response against conserved epitopes on a protein antigen, comprising:

(a) identifying a primary immunodominant epitope in the antigen;

(b) replacing at least one high LODrps amino acid in the primary immunodominant epitope with a low LODrps amino acid thereby significantly eliminating the antigenicity of the primary immunodominant epitope, to create a modified antigen; wherein the modified antigen induces antibodies against conserved epitopes. In some embodiments, at least one high LODrps amino acid from each primary immunodominant epitope is replaced with a low LODrps amino acid.

The method of invention is suitable for the manufacture of a vaccine. In related embodiments, the vaccine is used for immunization against a disease by administration of an antigen as described herein. In some embodiments, the prime and boost antigens are different.

In other embodiments, the invention includes a modified protein antigen in which a primary immunodominant epitope in the native protein antigen is modified by replacement of at least one high LODrps amino acid with a low LODrps amino acid, thereby significantly eliminating the antigenicity of the primary immunodominant epitope. This embodiment may be usefully applied to influenza antigens, such as HA Identification of the primary epitopes in influenza haemagglutinin (HA), and replacement of amino acids high on the log odds ratio propensity scale (LODrps) with corresponding low LODrps amino acids produces an HA molecule which induces antibody responses to conserved HA residues. Such modified HA molecules are suitable for a broadly neutralizing vaccine against influenza. Accordingly, the invention concerns an influenza haemagglutinin antigen in which all primary epitopes are modified to reduce antigenicity. In some embodiments, the haemagglutinin antigen is an H5 haemagglutinin.

Representative modifications include at Pro125, Ser129, Glu131, Pro140, Gln142, Lys144, Ser145, Lys156, Lys157, Asn158, Thr160, Arg166, Asp187, and/or Lys193 (H3 numbering). In some embodiments, the invention is an HA having one, two, three, four, five, six, seven, eight, nine, ten or all of these residues modified. Relatedly, the invention includes an influenza haemagglutinin antigen having a sequence at least 90%, 95, 98 and 99% identical with the HA portion found in any of SEQ ID NOs: 2-10.

Other suitable modifications may be grouped according to domains: d1 (P140, Q142, K144); d2 (K156, K157, N158), d3 (E131), d4 (D187, K193) and d5 (P125, R166). In some embodiments, one to eleven of these amino acids are mutated. In another embodiment, mutagenesis of all of d1-d5 may require only a single mutation in each domain.

Amino acids are replaced with low LODrps amino acids, such as alanine or threonine.

In related embodiments, the invention includes a vaccine, comprising one or more modified haemagglutinins and a pharmaceutically acceptable carrier. In some embodiments the haemagglutinins are proteins. Such proteins may be administered directly, or attached to carrier such as a virus-like particle, incorporated into a replication-defective viral particle or inactivated virus. In other embodiments, the vaccine is in the form of a nucleic acid (DNA, RNA, etc) which is administered to a subject, whereupon the haemagglutinin is expressed. "DNA immunization" is well known in the art.

The invention also includes a method of making an influenza vaccine, comprising
(a) identifying the primary epitopes on the HA molecule;
(b) replacing high LODrps amino acids in one or more primary epitope with low LODrps amino acids;
wherein the vaccine induces neutralizing antibodies that are cross-protective against distantly related HA molecules.

The invention also includes related methods of using the compositions of the invention. Accordingly, the invention includes a method of immunizing a subject, comprising administration of one or more doses of a vaccine made as described herein. In related embodiments, the subject is immunized with a composition comprising an antigen with an HA having modifications at Pro125, Ser 126, Ser129, Glu131, Pro140, Gln142, Lys144, Ser145, Lys156, Lys157, Asn158, Thr160, Arg166, Asp187, and/or Lys193; an antigen with an HA having modifications at Ser126, Ser129, Glu131, Pro140, Gln142, Lys144, Ser145, Lys156, Thr160, Arg166, Asp187, and/or Lys193, or an influenza haemagglutinin antigen having a sequence at least 90% identical with the HA portion found in any of SEQ ID NOs: 2-10. An immunization protocol may include immunization with more than one xHA together in a single dose, multiple doses, and multiple doses with different xHAs in each dose. An immunization protocol may include immunization with xHA and an adjuvant. Adjuvants, in the present context, include cytokines and other immunomodulatory molecules such as TLR (toll like receptor) agonists and their derivatives that stimulate the immune response.

In other embodiments, the xHA molecules may be bound to a structure that enhances the immune response, such as a virus-like particle, an immunostimulatory molecule (e.g. Tetanus toxin fragment), a dendrimer, and the like.

The HA molecules of the present invention are also suitable for the elicitation of antibodies that are broadly cross protective, including polyclonal and monoclonal antibodies. Such antibodies can provide "passive immunity" against infection and/or treatment of infected individuals. For example, such antibodies can be obtained, purified, concentrated, and stored. Accordingly, the invention includes methods of obtaining antibodies against the modified HA molecules, and antibodies obtained by immunization with such molecules.

The methods and compositions described herein are suitable for generation of an immune response against influenza viruses, especially influenza A, and are therefore used in a vaccine against influenza A infection.

Figure 1:
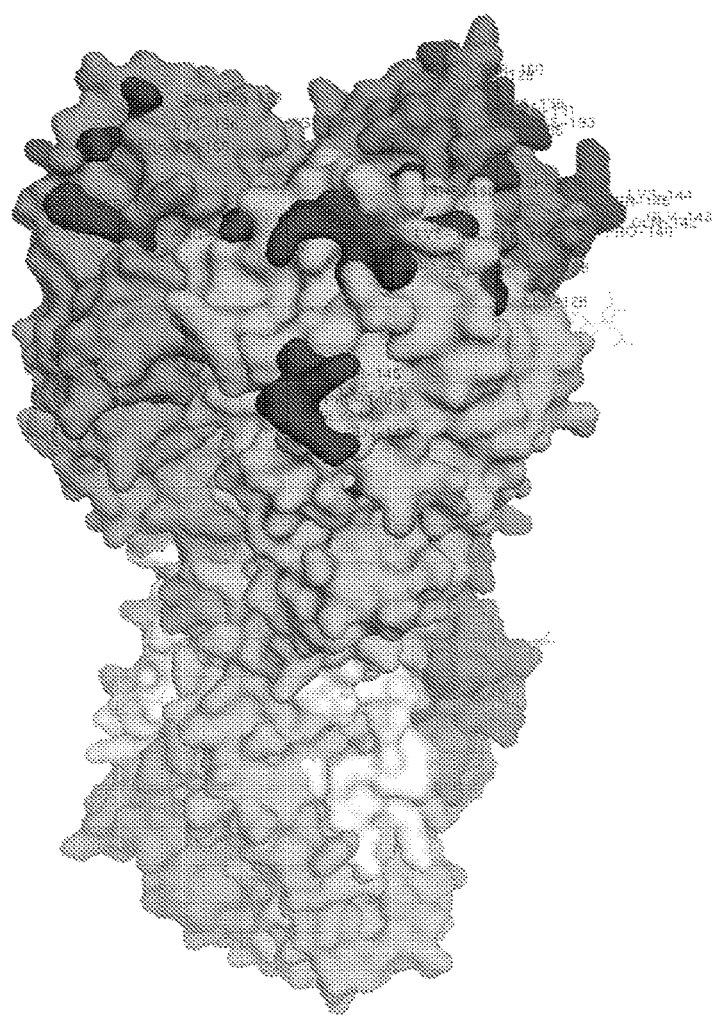
FIG. 1 shows the 2.9 Å 2FKO.pdb structure (Stevens, J., et al., *Structure and receptor specificity of the hemagglutinin from an H5N1 influenza virus*. Science, 2006. 312: p. 404-10) of the hemagglutinin from the A/Viet/1203/04 H5 influenza virus, with its monomeric subunits drawn in 3 different shades of gray.

The membrane-distal "head" of the trimeric HA is at the top of the illustrated molecule, and contains receptor binding and primary antigenic determinant structures. The membrane-proximal "stem" is at the bottom, and contains conserved fusion peptide and HA1/HA2 cleavage site sequences.

To create xHA antigens and shift the immune response from "head" primary antigenic determinants to conserved HA structures (including fusion-peptide CR6261 epitopes (white) on the HA stem (Ekiert, D. C., G. Bhabha, et al. (2009). "Antibody recognition of a highly conserved influenza virus epitope." *Science* 324(5924): 246-51)), up to 11 high LODrps amino acids in primary antigenic determinant(s) (black) were replaced with amino acids having lower Discotope LODrps values.

FIG. 2 illustrates the *Drosophila* Expression System (DES) (InVitrogen) construct for production of recombinant V1203 hemagglutinin and xHA production.

FIGS. 3a-d. Purified recombinant xHAs bearing mannosylated oligosaccharides for immune presentation 3a, Reduced and 3b, Non-reduced SDS-PAGE of purified xHAs (200 ng/lane) 3c, GNA lectin blot of duplicate of gel in a. GNA binds to terminal mannose 3d, Undigested (0) and PNGase F (P) digested xHAs. left, sypro red stained gel; right, GNA stained blot.

FIG. 4. Sequences of the parent hemagglutinin and xHAs.

The xHA.s were expressed in the *Drosophila* Expression System (InVitrogen) using the pmtbipv5hisa vector as shown in FIG. 2. Expressed polypeptides were comprised of: (1) the BIP signal sequence from pmtbipv5hisa, (2) followed by the dipeptide Arg-Ser from a Bgl2 linker sequence, (3) followed by HA0 encoding sequences incorporating (a) substitutions in primary antigenic determinant sites as indicated in Table 3, and (b) substitution of a "T" rather the "RRRKK"® sequence at the HA1/HA2 cleavage site of wildtype V1203, (4) followed by a polypeptide encoding a thrombin cleavage site, foldon sequence, and hexa-histidine sequence tag, after the KREEIS sequence of HA2.

The expressed parental and xHA hemagglutinin sequences are shown with the BIP signal sequence in three letter code, primary antigenic substitutions primary antigenic determinant substitutions indicated as bold underlined residues, and C-terminal thrombin-foldon-hexaHis polypeptide in bold. Italics indicate Xba I-Kpn I fragment used for rapid construction of the xHA variants.

FIG. 5: Immunoassays to verify proper folding of recombinant hemagglutinins and primary antigenic determinant knock out in xHAs.

FIG. 6 A-D Polyclonal antisera to xHAs contain antibodies that compete for binding of a conserved fusion peptide-containing epitope on the HA stem. Panel A shows no competition by mouse non-immune serum (m NI, open circles), and competitive, concentration-dependent reduction of 1F02 binding following exposure to the positive control C179 mAb (solid triangles). Each of the plots in the remaining B-D panels presents 1F02 competition results from serum samples obtained at various stages during the immunization of a single animal with xHAs. The designation "pr" indicates antisera obtained after priming, "b1" and "b2" are respectively antisera obtained after boosts 1 and 2, etc. The animals in panel B were primed and boosted with xHA.par (10 ug/injection). The animals in panels C and D, were primed with xHA.4b, then repeatedly boosted with xHA.5b; those in C received 10 ug doses of the xHA antigens, while those in D received 20 ug doses.

FIGS. 7a-7d Hemagglutination inhibition (HAI) by antisera to xHAs.

Hemaggutination inhibition assays were based on the standard W.H.O. kit protocol for Hemagglutination testing. Antisera were treated overnight at 37° C. with 3 volumes of receptor destroying enzyme (RDE, Denka), which was subsequently inactivated for 30 m at 56° C. Hemagglutination microplate wells were loaded with 25 ul of RDE-treated samples representing overall 18, 36 and 72-fold dilutions of the antisera, or with PBS. The four HA-pseudotyped lentviruses used for FIG. 2 HA neutralization assays were employed as 'antigens' in the HA inhibition assays. The LV antigen stocks were adjusted to 8 HA units/50 ul, and 25 ul (4 HA units) added to the antiserum- and PBS-containing wells. After 30 minutes of incubation, 50 ul of glutaraldehyde fixed 0.5% turkey RBCs (Fitzgerald) were added to the antiserum+LV incubations, and plates were photographed 40 min later.

DETAILED DESCRIPTION OF THE PREFERRED EMBODIMENTS

Because the primary immune response to influenza is directed against continuously evolving primary antigenic determinant structures on the hemagglutinin, the inventor has constructed a series of HA antigens in which these primary epitopes have been modified to ablate immunogenicity but keep overall structure of the HA. The resulting antigen molecule(s) thereby stimulate the production of antibodies against secondary antigenic determinants, which are epitopes that do not map to the primary antigenic determinants. Antibodies against conserved elements are broadly neutralizing.

To reduce uncertainty, the following definitions are used throughout:

"About" is used as understood by the person of ordinary skill in the context of the variable to which "about" is applied. When in doubt, "about" indicates a variation of ±10% of the stated value.

"Haemagglutinin" or "HA" refers to the Influenza haemagglutinin protein. In certain embodiments, this is the influenza A haemagglutinin, and recombinant variants thereof. In exemplary embodiments, the haemagglutinin is H5, or derived from H5. The term is used to describe a family of proteins, without regard to whether the protein actually possesses the property of haemagglutination. HAs are traditionally grouped by serotyping, into H1, H2, H3, H4, H5 and the like. The serotypes reflect antigenic and genetic variation. There is also variation within a given serotype, but this is less than between serotypes.

"xHA" refers to an HA for which one or more primary antigenic determinants are modified. "xHA.par" refers to the recombinant parental control hemagglutinin, which in the exemplary case is the HA from A/Vietnam/1203/2004 with the describe modification of the HA1/HA2 cleavage site.

"Antigenic determinants", or "epitopes," are structures recognized by antibodies and T-cell receptors of the immune system. Preferably, such epitopes are antibody epitopes. In the case of hemagglutinin, a small number of structures on the ectodomain (head) surface induce antibodies much more readily than the rest of the molecule and are referred to as being "immunodominant".

"Primary antigenic determinants" are synonymous with "immunodominant epitopes" and are those to which the immune response is primarily directed. If expressed numerically, an immune response that is at least one order of magnitude greater to a given epitope would indicate that it is immunodominant. In the context of influenza HA, those epitopes in the highly variable regions of the HA head to which the immune system normally develops the strongest antibody response, and which are recognized following infection or immunization with conventional seasonal flu vaccines, are the "primary antigenic determinants." These determinants in influenza are constantly evolving.

"Secondary antigenic determinants" are not immunodominant. In the context of the present invention, secondary antigenic determinants are those epitopes that are recognized after ablation of the primary antigenic determinants. Secondary antigenic determinants may be located in the conserved regions of the HA, which occur both on the HA head and stem. "Ablation" of antigenic determinants traditionally occurred by deletion of the entire epitope but is meant here to indicate ablation of antigenicity, by substitution of amino acids. Following from the immunodominant terminology, Secondary antigenic determinants may also be referred to as "immunorecessive."

"Escape mutant" refers to a derivative influenza virus that does not bind to, and/or is not neutralized by, a particular antibody or antiserum. As used herein, "escape mutant" refers to a virus containing a mutation in an epitope targeted by a neutralizing antibody.

"LODrps" is the "log odds ratio propensity scale" which measures the natural logarithm of the odds-ratio of a given amino acid to be present on the antigen side of an antigen-antibody interaction, and is therefore a measure of the likelihood of being an epitope. A high LODrps value means that the amino acid is over-represented in the set of structurally well-defined epitopes, whereas under-represented amino acids have low log-odds ratio values. The term LODrps is described in greater detail below.

A "vaccine" describes a preparation designed to induce an immune response that is protective against disease. In the present context, a vaccine induces an immune response against influenza virus. A vaccine may be prophylactic or preventative, given prior to or shortly after exposure to an influenza virus; or therapeutic, given during infection to boost the immune response or drive the response in a specific direction. A vaccine does not have to induce a fully protective response that prevents all disease, as not all vaccines produce an immune response in all people, and the strength and nature of the immune response varies between people.

"Antibody" as used herein encompasses natural antibodies, chimeric and recombinant antibodies, and antibody fragments, such as Fab, scFv, and the like.

An "adjuvant" increases the immune response against an antigen with which it is presented. Adjuvants are known in the art and include aluminium hydroxide, monophosphoryl lipid A, oils, cytokines, toll like receptor agonists, and the like.

Influenza Hemagglutinin Molecular Structure

HA is the major surface protein of the virus as well as the major viral target of neutralizing antibodies. The 2.9 Å 2FKO.pdb structure (Stevens, J., et al., *Structure and receptor specificity of the hemagglutinin from an H5N1 influenza virus*. Science, 2006. 312: p. 404-10) of the hemagglutinin from the A/Viet/1203/04 H5 influenza virus is shown in FIG. 1. It is a homotrimer with a large head (ectodomain) comprised of prominent beta sheet structures, and a stem (stalk) composed of long alpha helices. The base of the stem anchors the hemagglutinin in the viral membrane (or cellular membrane prior to budding), while its ectodomain head is exposed on the surface of the virus. HA plays an essential role in infection and the viral life cycle by (i) presenting binding sites for cellular receptors on its ectodomain surface and (ii) mediating fusion of viral and host-cell membranes to permit cellular entry of the genome-transcriptase complex following endocytosis.

Monomer subunits of the hemagglutinin trimer are synthesized as large HA0 precursor molecules, which are cleaved by host proteases at a site in the stem to generate HA1 and HA2 fragments of about 300 and 200 residues, respectively. The head is composed of HA1 sequences only, while the stem is a structurally complex structure containing entwined HA1 and HA2 sequences.

Naturally contracted influenza infections and seasonal flu vaccines elicit antibodies which bind primary antigenic determinant epitopes on the HA head. The primary antigenic determinants are located adjacent to the receptor binding sites. Accordingly, antibodies to primary antigenic determinants are neutralizing and block infection by restricting host cell sialic acid receptor access to the HA receptor binding site. However, the protective function of these antibodies is short-lived due to rapid evolution of primary antigenic determinants under selective pressure.

The primary antigenic determinants on HA have been identified by sequencing "escape mutants" selected with neutralizing antibodies, and correspond to hot spots of sequence variation during virus evolution (Stevens, J., et al., *Structure and receptor specificity of the hemagglutinin from an H5N1 influenza virus*. Science, 2006. 312: p. 404-10, Kaverin, N., et al., *Structure of antigenic sites on the haemagglutinin molecule of H5 avian influenza virus and phenotypic variation of escape mutants*. J Gen Virol., 2002. 83: p. 2497-505, Kaverin, N. V., et al., *Epitope mapping of the hemagglutinin molecule of a highly pathogenic H5N1 influenza virus by using monoclonal antibodies*. J Virol, 2007. 81(23): p. 12911-7, Philpott, M., et al., *Hemagglutinin mutations related to attenuation and altered cell tropism of avirulent avian influenza A virus*. J Virol., 1990. 64: p. 2941-7, Wiley, D., I. Wilson, and J. Skehel, *Structural identification of the antibody-binding sites of Hong Kong influenza haemagglutinin and their involvement in antigenic variation*. Nature, 1981. 289: p. 373-8.). FIG. 1 shows the locations (black) of H5 HA primary antigenic determinants identified using avian H5 escape mutant data and sequence information from human H5 drift isolates obtained during 1997-2004. The primary antigenic determinants surround and overlap the receptor binding domain (RBD) (Stevens, J., et al., *Structure and receptor specificity of the hemagglutinin from an H5N1 influenza virus*. Science, 2006. 312: p. 404-10, Weis, W., et al., *Structure of the influenza virus haemagglutinin complexed with its receptor, sialic acid*. Nature, 1988. 333: p. 426-31), which mediates binding of the virus to the cell during infection. A RBD and adjacent primary antigenic determinants are present on each monomer of the HA trimer.

In addition to the well known, narrowly-focused antibodies to the continuously evolving primary antigenic determinants on the HA head, there are also broadly-protective antibodies that recognize evolutionarily conserved and functionally critical structures located on HA stem and head surfaces.

For example, mAbs C179, CR6261, F10 and 1F02 (see, e.g., Okuno J Virol., 1993. 67: p. 2552-8; Ekiert et al. Science. 324 (2009); Sui Virology 387: 473-481 (2009); Wrammert et al. J Exp Med, 2011. 208(1): 181-93) recognize fusion peptide-containing HA stem epitopes that are conserved in Group 1 influenzas, which include the H1, H2, H5 subtypes. Similarly, mAb CR8020 recognizes a fusion peptide-containing HA stem epitope conserved in Group 2 influenzas, which includes the H3 and H7 subtypes (Ekiert et al. Science. 2011. 333:843-50). Finally mAb FI6 recognizes fusion peptide-containing HA stem epitopes from both Group 1 and Group 2 viruses (Corti, D. et al., Science, 2011. 333:850-6).

In addition to the broadly-protective antibodies recognizing conserved fusion-peptide containing structures located on HA stem, there are also broadly neutralizing antibodies that recognize conserved structures on the HA head (Khurana, *Antigenic fingerprinting of H5N1 avian influenza using convalescent sera and monoclonal antibodies reveals potential vaccine and diagnostic targets*. PLoS Med, 2009. 6(4): p. e1000049; Krause et al, *A broadly neutralizing human monoclonal antibody that recognizes a conserved, novel epitope on the globular head of influenza H1N1 virus hemagglutinin*. J Virol, 2011. pmid_21849447; Whittle et al. *Broadly neutralizing human antibody that recognizes the receptorbinding pocket of influenza virus hemagglutinin*. Proc Natl Acad Sci USA, 2011. 108(34): p. 1421621; Yoshida et al., *Crossprotective potential of a novel monoclonal antibody directed against antigenic site B of the hemagglutinin of influenza A viruses*. PLoS Pathog, 2009. 5(3): p. e1000350).

The inventor hypothesized that reducing the immunogenicity of H5 HA primary antigenic determinants will increase immune responses against conserved HA epitopes that do not efficiently elicit immunological memory antibodies under routine infection and seasonal flu vaccine immunization conditions. These conserved epitopes are present in a broad spectrum of influenzas, and more likely to be retained in future H5N1 viruses than are the rapidly evolving primary antigenic determinants targeted by conventional vaccines, and therefore should represent superior targets for generating broad H5 and heterosubtypic cross-protection across all HAs.

B-cell epitope characteristics The H5 HA primary antigenic determinants to be neutralized in this work are defined based on extensive escape mutant and genetic drift data. However, in order to successfully knock them out and avoid their undesirable replacement with novel antigenic determinants, it is necessary to consider the properties of B-cell epitopes. Generally, B-cell epitopes locate to hydrophilic and dynamically flexible sites on a protein's surface (reviewed in Haste Andersen, P., M. Nielsen, and O. Lund, Prediction of residues in discontinuous B-cell epitopes using protein 3D structures. Protein Sci, 2006. 15(11): p. 2558-67, Parker, J. M., D. Guo, and R. S. Hodges, New hydrophilicity scale derived from high-performance liquid chromatography peptide retention data: correlation of predicted surface residues with antigenicity and X-ray-derived accessible sites. Biochemistry, 1986. 25(19): p. 5425-32, Ponomarenko, J. V. and P. E. Bourne, Antibody-protein protein interactions: benchmark datasets and prediction tools evaluation. BMC Struct Biol, 2007. 7: p. 64; Jin L, Fendly B M, Wells J A, High resolution functional analysis of antibody-antigen interactions. J Mol Biol. 1992 Aug. 5; 226(3):851-65.). The recent exponential growth of antigen-antibody complex structures in the Protein Data Base enables detailed analysis of antigen-antibody contact sites and provides new information about the properties of surface substructures that form epitopes on protein antigens. Table 1 is an epitope log-odds ratio propensity scale (LODrps) derived by analyzing the distribution of amino acids present on the antigen side of antigen-antibody interfaces in 76 different x-ray structures of antigen-antibody complexes (Haste Andersen, P., M. Nielsen, and O. Lund, Prediction of residues in discontinuous B-cell epitopes using protein 3D structures. Protein Sci, 2006. 15(11): p. 2558-67.).

TABLE I

| epitope log odds ratios for 20 amino acids | | | |
|---|---|---|---|
| N | 1.242 | Y | 0.03 |
| R | 1.18 | W | −0.064 |
| P | 1.164 | S | −0.145 |
| K | 1.136 | T | −0.233 |
| H | 1.098 | I | −0.713 |
| Q | 1.082 | F | −1.147 |
| D | 0.691 | V | −1.474 |
| E | 0.346 | A | −1.522 |
| M | 0.273 | L | −1.836 |
| G | 0.189 | C | −3.519 |

A high Discotope log-odds value means that the amino acid is over-represented in the set of structurally well-defined epitopes, whereas under-represented amino acids have low log-odds ratio values. The epitope log-odds ratio propensity scale is particularly useful when considered in conjunction with the extensive evolutionary drift and escape mutant mapping data available for influenza hemagglutinins.

Of the ten H5 hemagglutinin residues identified as primary antigenic determinants on the basis of drift and escape mutant evidence, i.e., empirically, seven had positive log-odds ratios.

The invention utilizes the epitope log-odds ratio propensity scale in the design of x-HA mutants with neutralized primary antigenic determinants. The strategy for reducing H5 HA primary epitope immunogenicity is to replace primary antigenic determinant residues for which there is strong drift and escape mutant evidence with amino acids that have lower log-odds ratios. This will not only destroy primary epitope(s), but should also reduce the likelihood of the new surface(s) serving as antigenic determinants. Without being bound by theory, it is believed that by disfavoring clonal selection of B cells for primary antigenic determinants, the immune response should be shifted to secondary epitopes, including conserved epitopes which do not normally elicit immune responses due to the immunodominance of HA primary antigenic determinants.

The invention is further understood by reference to the following examples, which are representative and not limiting.

EXAMPLES

Example 1. Hemagglutinin Expression and Purification

Recombinant influenza hemagglutinins produced by two different baculovirus-based insect cell expression strategies have been demonstrated to be suitable for vaccine trials (Treanor, J. J., et al., Dose-related safety and immunogenicity of a trivalent baculovirus-expressed influenza-virus hemagglutinin vaccine in elderly adults. J Infect Dis, 2006. 193(9): p. 1223-8) and for high-resolution receptor binding and structural studies (Stevens, J., et al., Structure and receptor specificity of the hemagglutinin from an H5N1 influenza virus. Science, 2006. 312: p. 404-10, Stevens, J., et al., Structure of the uncleaved human H1 hemagglutinin from the extinct 1918 influenza virus. Science, 2004. 303: p. 1866-70.). Accordingly, baculovirus expression systems are appropriate for the expression of HA antigens.

The constructs of Stevens contain C-terminal foldon sequences to mediate correct folding of the HA, leading to crystallographically verified trimeric HAs, an improvement over the original baculovirus-expressed Protein Sciences HAs of the Treanor reference. Accordingly, the DES expression approach used, below, is based on the Stevens constructs that contain the foldon domain.

A different insect cell expression system, the Drosophila Expression System (DES) (InVitrogen) was used for production of control hemagglutinins and xHAs described in the Examples. The DES parent construct for parental H5N1 A/Vietnam/1203/2004 (V1203) hemagglutinin production is illustrated in FIG. 2. The sequence of the expressed recombinant hemagglutinin is SEQ ID NO: 1 of FIG. 4. The DNA sequence encoding this protein was inserted into pMT/BiPN5-His vector, obtained from Invitrogen Corp. The V1203 HA0 precursor sequence was placed downstream of a metallothionein promoter for inducible expression, and a BIP signal peptide to mediate secretion. A thrombin cleavage site and 30-residue foldon and hexahistidine sequences were placed C-terminal to the hemagglutinin-encoding sequence to facilitate HA trimerization, purification and the subsequent removal of the foldon and his tag. The site of HA0 cleavage into HA1 and HA2 was modified (PQR-ERRRKKRGLFG to PQRETRGLFG) in order to maintain the prefusion conformation, reduce HA cleavage, and promote the production of HA0 oligomers and trimers, which exhibit superior immunogenicity (Wei, C. J., et al., *Comparative efficacy of neutralizing antibodies elicited by recombinant hemagglutinin proteins from avian H5N1 influenza virus.* J Virol, 2008. 82(13): p. 6200-8.). The HA1 region in which the primary antigenic determinants are located is shown in a magnification, with the positions of the eleven primary antigenic determinant residues targeted by our study marked by black X marks. These primary antigenic determinant residues were selected on the basis of escape mutant data, genetic drift data, and Discotope high log odds values, as explained in Example 2, Table 2.

The HA0 DNA sequence of the construct was optimized for expression in the DES *Drosophila* expression system by employing frequently utilized codons from a data base of highly expressed *Drosophila* proteins (Shields, D. C., et al., "*Silent*" *sites in Drosophila genes are not neutral: evidence of selection among synonymous codons.* Mol Biol Evol, 1988. 5(6): p. 704-16.). The DNA sequence was further modified to include translationally silent, unique restriction sites at the locations shown in the map. Restriction sites in the magnified primary antigenic determinant region were utilized for rapid, efficient and economic substitution of cassettes with changes for x-HA variants.

Expression and Purification of V1203 Hemagglutinin and Related HAs

DES-expressed control hemagglutinins and xHAs were purified using the strategy described by Stevens and Wilson (Stevens, J., et al., *Structure and receptor specificity of the hemagglutinin from an H5N1 influenza virus.* Science, 2006. 312: p. 404-10, Stevens, J., et al., *Structure of the uncleaved human H1 hemagglutinin from the extinct 1918 influenza virus.* Science, 2004. 303: p. 1866-70.). This protocol produces HAs that are properly folded with polymerization into trimers resembling those obtained from bromelain-released virus hemagglutinin. Thus, such HAs mimic naturally occurring HAs.

The expression system used in the present examples features a thrombin cleavage site C-terminal to the HA0 sequence, followed by a "foldon" sequence to promote efficient assembly of the trimer (Frank, S., et al., *Stabilization of short collagen-like triple helices by protein engineering.* J Mol Biol, 2001. 308: p. 1081-9), and finally a hexa His-tag to facilitate protein purification. Expression plasmids were DNA sequence verified for the region encoding the signal sequence cleavage site through the His-tag and stop codon, then co-transfected with pCoHygro (InVitrogen) or pCoPuro (Iwaki, T., et al., *Rapid selection of Drosophila S2 cells with the puromycin resistance gene.* Biotechniques, 2003. 35(3): p. 482-4, 486) selection plasmids into *Drosophila* S2 cells. Stably transformed hemagglutinin-expressing cell lines were selected by growth in the presence of hygromycin or puromycin for several weeks.

Stably transfected, hemagglutinin-expressing S2 cell lines were expanded up to 500 ml in 10% serum-containing Express Five media (InVitrogen). Then cultures were adapted to serum-depleted conditions by 1:1 dilution with serum-free media up to 2 liters. HA expression from the metallothionein promoter was induced by addition of $CuSO_4$, and conditioned medium harvested 3-4 days later at trypan blue cell viabilities of 80-90%. Conditioned media supernatants were prepared, and frozen at −20 C for cryoprecipitation of insect ferritin and storage. The xHAs were purified by Ni-NTA (Qiagen) chromatography with imidazole gradient elution. Peak fractions, identified by SDS-PAGE, were pooled, buffer exchanged and concentrated into 50 mM NaCl, 10 mM Tris pH 8. Protein concentration was measured by Coomassie Blue dye binding (Biorad). The xHAs used in this study were not thrombin digested, and retained the C-terminal foldon/his-tag sequence to promote recovery of trimeric and oligomeric hemagglutinins, which are efficient immunogens (Wei et al, J. Virol., 2008, 82:6200). Yields of ~0.5 mg or more of hemagglutinin per liter of induced cells were obtained. Reducing and non-reducing SDS-PAGE was performed to assess purity and confirm HA0 status, and the content of monomeric, trimeric and multimeric xHAs assessed by size exclusion chromatography on Sephacryl-S300 HR.

Figure 3:
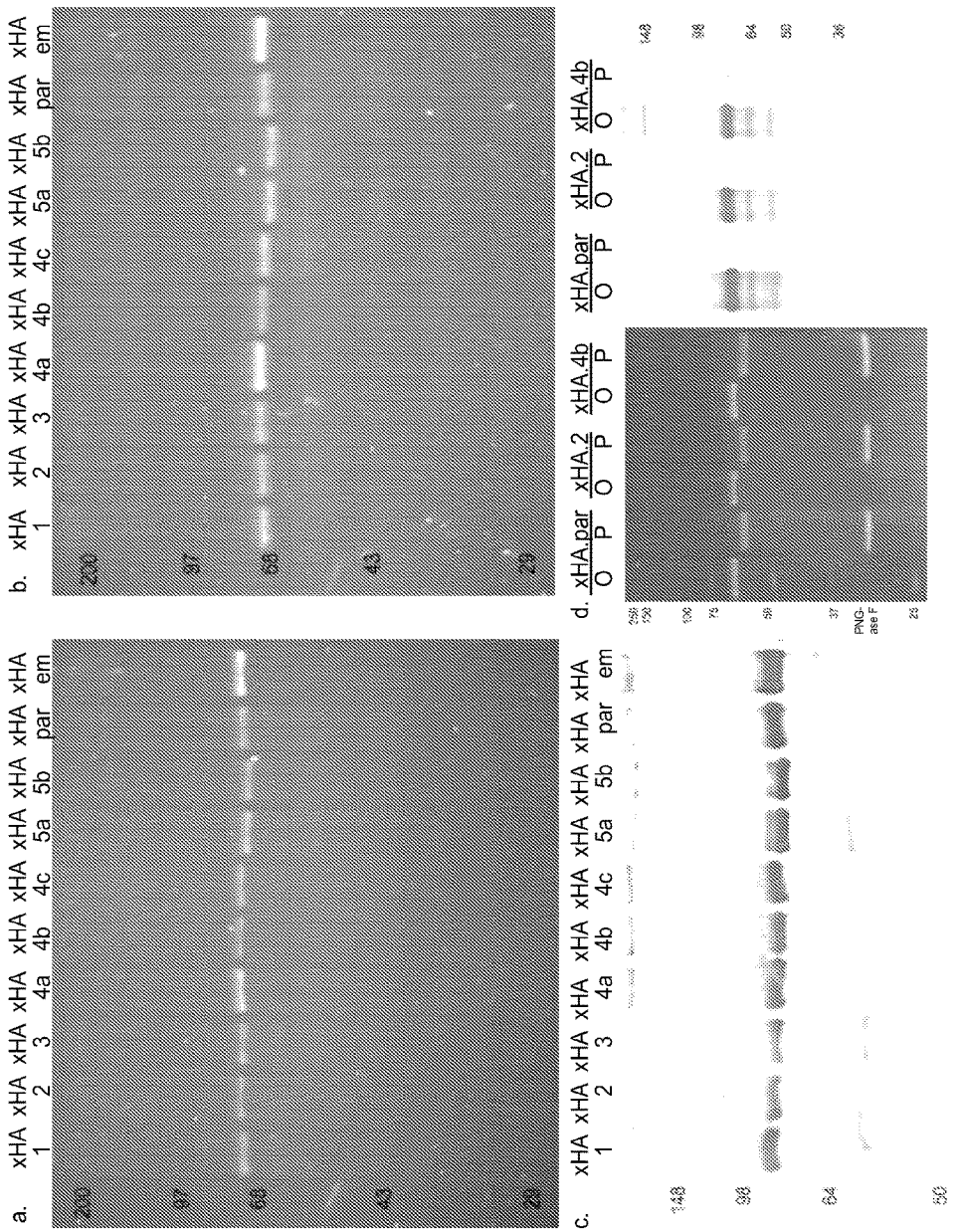

The above DES expression and purification protocols supported efficient production of 70 kD HA0 parental V1203 HA and xHAs, which are assembled into trimeric hemagglutinins. FIG. 3 panel a and b show reduced and non-reduced SDS-PAGE gels, demonstrating the high level of purity of the purified xHA antigens, and the absence of inter-HA0 disulfide bonding, which would be indicative of misfolding. Further evidence for the proper folding of the recombinant xHAs was provided by patterns of binding to (1) the 1F02 mAb to the fusion-peptide containing epitope on the HA stem (Wrammert et al., J Exp Med, 2011. 208:181) and (2) the VN04 panel of mapped mAb antibodies to V1203 HA primary antigenic determinant continuous and discontinuous epitopes (Kaverin et al., J Virol, 2007, 81:12911). (1F02 and VN04 mAb binding data is presented below in Example 2, FIG. 5.) The purified xHAs migrated on S300 Sephacryl gel exclusion chromatography as ~200 kD trimers and higher MW multimers, as previously described for baculovirus-expressed HAs (Stevens et al., Science, 2004, 303:1866-70; Wei et al., J. Virol., 2008, 82:6200).

Production of xHAs antigens in *Drosophila* S2 cells is believed to results in their N-glycosylation with paucimannose and related glycans (Kim Y K, et al., Production and N-glycan analysis of secreted human erythropoietin glycoprotein in stably transfected Drosophila S2 cells. Biotechnol Bioeng. 2005 Nov. 20; 92(4):452-61). Such glycosylation may be advantageous for efficient presentation of these molecules to the immune system via macrophage, monocyte and dendritic cell mannose receptors (Buzás E I et al., Carbohydrate recognition systems in autoimmunity. Autoimmunity. 2006 December; 39(8):691-704; Gazi, U. and L. Martinez-Pomares, Influence of the mannose receptor in host immune responses. Immunobiology, 2009. 214(7): p. 554-61). FIGS. 2*c* and 2*d* GNA lectin blotting and PNGase F digestion experiments confirmed the presence of mannose terminated Nglycans on the xHAs.

These results demonstrate successful *Drosophila* expression system synthesis and purification of recombinant hemagglutinins for induction of antisera and evaluation of the immune responses.

Example 2. Design and Production of xHa Mutants

V1203 primary antigenic determinants were ablated in x-HA variants by substitutions at epitope residues identified on the basis of escape mutant and genetic drift data. These positions were replaced with amino acids that are present at low frequencies on the antigen side of contact sites in a database of antigen-antibody crystal structures. Knockout of V1203 specific primary antigenic determinants in xHA variants was verified by screening against a panel of well-characterized monoclonal antibodies (Kaverin et al., J Virol, 2007, 81:12911) obtained from the Biodefense and Emerging Infections Research (BEIR) repository.

Mapping of the Primary Antigenic Determinants.

The first step in the design of the xHAs was to carefully analyze H5N1 antigenic drift and escape mutant data and to develop operational definitions of the primary antigenic determinants that will be knocked out. Table 2 presents the H5 A/Viet/1203/04 HA 1 ectodomain sequence from residues 125-209 (H3 numbering), with primary antigenic determinant residues identified by symbols in front of the residue ID number. "%" indicates primary antigenic determinant residues for which differences from the A/Viet/1203/04 sequence have been observed both in laboratory-generated escape mutants and in natural drift isolates (human viruses, 1997-2004). "$" indicates residues for which the assignment as a primary antigenic determinant was made solely on the basis of escape mutant evidence. "#" indicates residues for which there is only evolutionary drift evidence.

TABLE 2

MAPPING OF H5 HEMAGGLUTININ PRIMARY ANTIGENIC DETERMINANTS
(Table discloses residues 138-225 of SEQ ID NO: 1)

| [1] residue ID | [2] by drift (hum) | [3] by drift (all) | [4] by mAb escape | [5] by escape from mAb VN04- | | | | | | | [6] by Discotope |
|---|---|---|---|---|---|---|---|---|---|---|---|
| | | | | 2 | 8 | 9 | 10 | 13 | 15 | 16 | |
| #125 PRO* | | | A | | | | | | | | |
| 125A LYS* | | | | | | | | | | | |
| #125B SER | H | | | | | | | | | | D |
| $126 SER | | | | | x | | | | | | D |
| 127 TRP | | | | | | | | | | | |
| 128 SER | | | | | | | | | | | D |
| %129 SER | H | A | M | X | | X | | X | X | X | D |
| 130 HIS | | | | | | | | | | | |
| %131 GLU* | H | | M | | | | X | X | X | X | |
| #132 ALA | H | | | | | | | | | | |
| $133 SER | | | M | | | | | | | | |
| #133A LEU | H | A | | | | | | | | | |
| 134 GLY | | | | | | | | | | | |
| #135 VAL | H | | | | | | | | | | |
| 136 SER | | | | | | | | | | | |
| #137 SER | H | | | | | | | | | | |
| #138 ALA | H | | | | | | | | | | |
| 139 CYS | | | | | | | | | | | |
| %140 PRO* | H | | M | X | | X | | X | X | X | |
| 141 TYR | | | | | | | | | | | |
| %142 GLN* | H | A | M | | X | X | | X | X | | D |
| %143 GLY | H | | | x | | | | x | | | D |
| %144 LYS* | H | A | M | x | | | | xX | | | |
| %145 SER | | A | M | x | | X | xX | xX | X | | |
| 146 SER | | | | | | | | | | | |
| 147 PHE | | | | | | | | | | | |
| 148 PHE | | | | | | | | | | | |
| 149 ARG* | | | | | | | | | | | |
| 150 ASN* | | | | | | | | | | | |
| 151 VAL | | | | | | | | | | | |
| 152 VAL | | | | | | | | | | | |
| 153 TRP | | | | | | | | | | | |
| 154 LEU | | | | | | | | | | | |
| $155 ILE | | | | x | | | | | | | |
| $156 LYS | | | M | X | | xX | xX | X | X | xX | |
| $157 LYS* | | | M | | | | | | | | |
| #158 ASN* | | | A | | | | | | | | D |
| #159 SER | H | | A | | | | | | | | D |
| %160 THR | H | | A | | | | x | | x | | D |
| 161 TYR | | | | | | | | | | | |
| 162 PRO* | | | | | | | | | | | D |
| #163 THR | | | A | | | | | | | | D |
| 164 ILE | | | | | | | | | | | D |
| 165 LYS* | | | | | | | | | | | D |
| %166 ARG* | | | A | x | | | | | | | D |
| 167 SER | | | | | | | | | | | D |
| 168 TYR | | | | | | | | | | | |
| 169 ASN* | | | | | | | | | | | |
| 170 ASN* | | | | | | | | | | | |
| 171 THR | | | | | | | | | | | |
| 172 ASN* | | | | | | | | | | | |
| 173 GLN* | | | | | | | | | | | |
| 174 GLU* | | | | | | | | | | | |
| 175 ASP* | | | | | | | | | | | |
| 176 LEU | | | | | | | | | | | |
| 177 LEU | | | | | | | | | | | |
| #178 VAL | | | A | | | | | | | | |
| #179 LEU | H | | | | | | | | | | |
| 180 TRP | | | | | | | | | | | |
| 181 GLY | | | | | | | | | | | |

TABLE 2-continued

MAPPING OF H5 HEMAGGLUTININ PRIMARY ANTIGENIC DETERMINANTS
(Table discloses residues 138-225 of SEQ ID NO: 1)

| [1] residue ID | [2] by drift (hum) | [3] by drift (all) | [4] by mAb escape | [5] by escape from mAb VN04- | | | | | | | [6] by Discotope |
|---|---|---|---|---|---|---|---|---|---|---|---|
| | | | | 2 | 8 | 9 | 10 | 13 | 15 | 16 | |
| 182 ILE | | | | | | | | | | | |
| #183 HIS* | H | | | | | | | | | | |
| 184 HIS* | | | | | | | | | | | |
| #185 PRO* | | A | | | | | | | | | |
| 186 ASN* | | | | | | | | | | | D |
| $187 ASP* | | | | | | x | | | | | D |
| 188 ALA | | | | | | | | | | | D |
| $189 ALA | | | M | | | | | | | | D |
| 190 GLU* | | | | | | | | | | | D |
| 191 GLN* | | | | | | | | | | | |
| #192 THR | H | | | | | | | | | | D |
| %193 LYS* | H | A | | | | x | | x | | | D |
| 194 LEU | | | | | | | | | | | |
| 195 TYR | | | | | | | | | | | |
| 196 GLN* | | | | | | | | | | | |
| 197 ASN* | | | | | | | | | | | D |
| 198 PRO* | | | | | | | | | | | D |
| 199 THR | | | | | | | | | | | D |
| #200 THR | H | | | | | | | | | | |
| 201 TYR | | | | | | | | | | | |
| #202 ILE | H | | | | | | | | | | |
| 203 SER | | | | | | | | | | | |
| 204 VAL | | | | | | | | | | | |
| 205 GLY | | | | | | | | | | | |
| 206 THR | | | | | | | | | | | |
| 207 SER | | | | | | | | | | | D |
| 208 THR | | | | | | | | | | | |
| 209 LEU | | | | | | | | | | | |

Footnotes for Table 2
[1] H5 A/Viet/1203/04 HA residue ID; H3 numbering
[2] H = Primary antigenic determinant assignment based on drift in 1997-2005 H5N1 human isolates, Stevens, 2006, FIG. S5 (Stevens, J., O. Blixt, et al. (2006). "Structure and receptor specificity of the hemagglutinin from an H5N1 influenza virus." Science 312(5772): 404-10.)
[3] A = Primary antigenic determinant assignment based on drift in 2003-2006 H5N1 human and avian isolates, Kaverin, 2007, Table 4 (Kaverin, N. V., I. A. Rudneva, et al. (2007). "Epitope mapping of the hemagglutinin molecule of a highly pathogenic H5N1 influenza virus by using monoclonal antibodies." J Virol 81(23): 12911-7.)
[4] M = Primary antigenic determinant assignment based on escape mutants of H5N2 A/Mallard/Pennsylvania/10218/84 from various mAbs, Kaverin, 2002, Table 3 (Kaverin, N., et al. (2002). "Structure of antigenic sites on the haemagglutinin molecule of H5 avian influenza virus and phenotypic variation of escape mutants." J Gen Virol. 83: 2497-505.)
[5] x = Primary antigenic determinant assignment based on escape mutants of H5 A/Vietnam/1203/04 from indicated monoclonal antibody, Kaverin, 2007, Tables 1 and 2
X = Primary antigenic determinant assignment based on H5N2 A/Mallard/Pennsylvania/10218/84 escape mutants (Kaverin, 2002) with the indicated mAb.
[6] D = predicted using DiscoTope algorithm for the identification of discontinuous B-cell epitopes, Haste Andersen, 2006 www.cbs.dtu.dk/services/DiscoTope
* Asterisks mark amino acids with epitope log odds ratio values of >0.3 (Haste Andersen, P., M. Nielsen, et al. (2006). "Prediction of residues in discontinuous B-cell epitopes using protein 3D structures." Protein Sci 15(11): 2558-67.)

Symbols in front of the residue ID number show primary antigenic determinant residues. Assignments were based on drift and escape mutant evidence ("%"), drift-only evidence ("#"), or escape mutant only data ("$").

The baculovirus expressed H5 A/Viet/1203/04 HA of Stevens (2006) is N-glycosylated on Asn-169 but not Asn-158.

Ablation of Primary Antigenic Determinants

Discotope log odds ratio propensity scale (LODrps) values for the 20 amino acids have been assigned based their relative frequencies on the antigen side of the antigen-antibody interfaces in 76 different x-ray structures (Haste Andersen, P., M. Nielsen, and O. Lund, Prediction of residues in discontinuous B-cell epitopes using protein 3D structures. Protein Sci, 2006. 15(11): p. 2558-67). A high LODrps means that the amino acid is over-represented in known, structurally well-defined epitopes, whereas under-represented amino acids have low LODrps values.

In the above Table 2 presentation of H5 HA primary antigenic determinant sequences, residues with high LODrps values are marked with asterisks (*). Of the 34 primary antigenic determinant residues identified with symbols in front of the residue ID number in Table 2, 11 are surface-exposed and have log-odds ratio values of >0.3. The inventor hypothesizes that replacing these residues with low or negative log-odds ratio amino acids (see Table 3) should not only knock out primary antigenic determinants, but also reduce the likelihood of the modified surfaces also serving as new antigenic determinants.

TABLE 3

DESIGN PLAN FOR PRIMARY ANTIGENIC DETERMINANT KNOCK-OUT IN CONTROL AND x-HEMAGGLUTININS

| V1203 control HA | escape mutant substitution(s) [1] | x-HA.em [4] | x-HA.Indo05 | x-HA.Egypt06 | x-HA.1 | x-HA.2 | x-HA.3 | x-HA.4a | x-HA.4b | x-HA.4c | x-HA.5a | x-HA.5b |
|---|---|---|---|---|---|---|---|---|---|---|---|---|
| S126 [2] (−0.145) [3] | Y (0.03) | S126Y (0.03) | S126 (−1.145) | S126 (−1.145) | S126 (−1.145) | S126A (−1.522) | S126 (−1.145) | S126 (−1.145) | S126 (−1.145) | S126 (−1.145) | S126A (−1.522) | S126A (−1.522) |
| S129 (−0.145) | D (0.691) | S129D (0.691) | S129D (0.691) | S129D (0.691) | S129 (−0.145) | S129 (−0.145) | S129 (−0.145) | S129 (−0.145) | S129 (−0.145) | S129 (−0.145) | S129A (−1.522) | S129A (−1.522) |
| E131 (0.346) | N (1.242) | E131N (1.242) | E131 (0.346) | E131 (0.346) | E131 (0.346) | E131 (0.346) | E131 (0.346) | E131 (0.346) | E131 (0.346) | E131 (0.346) | E131T (−0.233) | E131T (−0.233) |
| P140 (1.164) | L (−1.836) | P140L (−1.836) | P140 (1.164) | P140 (1.164) | P140 (1.164) | P140 (1.164) | P140 (1.164) | P140L (−1.836) | P140L (−1.836) | P140L (−1.836) | P140L (−1.836) | P140L (−1.836) |
| Q142 (1.062) | K (1.136) | Q142K (1.136) | Q142L (−1.836) | Q142 (1.062) | Q142 (1.062) | Q142 (1.062) | Q142 (1.062) | Q142K (1.136) | Q142T (−0.233) | Q142A (−1.522) | Q142T (−0.233) | Q142A (−1.522) |
| G143 (0.189) | E (0.346) | G143E (0.346) | G143 (0.189) | G143 (0.189) | G143 (0.189) | G143 (0.189) | G143 (0.189) | G143 (0.189) | G143 (0.189) | G143 (0.189) | G143 (0.189) | G143 (0.189) |
| K144 (1.136) | E (0.346) | K144E (0.346) | K144S (−0.145) | K144R (1.18) | K144T (−0.233) | K144 (1.136) | K144 (1.136) | K144E (0.346) | K144T (−0.233) | K144A (−1.522) | K144T (−0.233) | K144A (−1.522) |
| S145 (−0.145) | F (−1.147), P (1.164), T (−0.233) | S145F (−1.147) | S145P (1.164) | S145 (−0.145) | S145 (−0.145) | S145 (−0.145) | S145 (−0.145) | S145 (−0.145) | S145 (−0.145) | S145 (−0.145) | S145A (−1.522) | S145A (−1.522) |
| I155 (−0.713) | T (−0.233) | I155T (−0.233) | I155 (−0.173) | I155 (−0.173) | I155 (−0.173) | I155 (−0.173) | I155 (−0.173) | I155 (−0.173) | I155 (−0.173) | I155 (−0.173) | I155 (−0.173) | I155 (−0.713) |
| K156 (1.136) | E (0.346), N (1.242) | K156E (0.346) | K156 (1.136) | K156 (1.136) | K156 (1.136) | K156 (1.136) | K156A (−1.522) | K156E (−0.346) | K156T (−0.233) | K156A (−1.522) | K156T (−0.233) | K156A (−1.522) |
| T160 (−0.233) | A (−1.522) | T160A (−1.522) | T160 (−0.233) | T160A (−1.522) | T160 (−0.233) | T160 (−0.233) | T160 (−0.233) | T160 (−0.233) | T160 (−0.233) | T160 (−0.233) | T160A (−1.522) | T160A (−1.522) |
| R166 (1.18) | G (0.189) | R166G (0.189) | R166K (1.136) | R166 (1.18) | R166 (1.18) | R166T (−0.233) | R166 (1.18) | R166G (0.189) | R166A (−1.522) | R166A (−1.522) | R166A (−1.522) | R166A (−1.522) |
| D187 (0.691) | N (1.242) | D187 (0.691) | D187 (0.691) | D187 (0.691) | D187 (0.691) | D187 (0.691) | D187 (0.691) | D187 (0.691) | D187 (0.691) | D187 (0.691) | D187 (0.691) | D187 (0.691) |
| K193 (1.136) | E (0.346) | K193E (0.346) | K193R (1.18) | K193R (1.18) | K193 (1.136) | K193 (1.136) | K193 (1.136) | K193E (0.346) | K193T (−0.233) | K193A (−1.522) | K193T (−0.233) | K193A (−1.522) |
| LODrps Index [5] | | 0.06 | 4.6 | 6.3 | 3.9 | 3.9 | 4.0 | 0.4 | −3.2 | −9.6 | −9.2 | −15.6 |

6.7

[1] Escape mutant substitutions are shown in bold face for A/Vietnam/1203/04 (H5N1) escape mutants, and in italics for A/Mallard/Pennsylvania/10218/84 (H5N2) escape mutants
[2] H3 numbering is used throughout the Table.
[3] Log odds ratio propensity score (LODrps) value is in parentheses.
[4] Wildtype H5 A/Viet/1203/04 residues are shown in white cells, and substitution mutations are in gray cells.
[5] LODrps index was calculated from sum of Discotope LODrps scores of HA primary antigenic determinant residues. Higher values indicate that primary antigenic determinants are richer in amino acids that occur commonly on the antigen side of antibody-epitope contact sites. Lower values indicate that primary antigenic determinants are composed of amino acids which are under represented on the antigen side of antibody-epitope contact sites.

x-HA Design

Table 3 summarizes the design of H5 x-HA antigens. The parent molecule was HA0 from A/Viet/1203/04 (clade 1), a highly pathogenic H5N1 influenza isolated from a Vietnamese patient in 2004. A/Indonesia/5/05 (clade 2.1.3) and A/Egypt/2782/06 (clade 2.2) hemagglutinins serve as drift controls.

For a given macromolecular antigen, and especially for influenza hemagglutinins, some substructures stimulate immune responses very effectively, while other substructures do not. The common properties of protein substructures that are effective B-cell antigens include surface location, hydrophilicity and dynamic flexibility (Haste Andersen, P., et al., *Prediction of residues in discontinuous B-cell epitopes using protein 3D structures*. Protein Sci, 2006. 15(11): p. 2558-67, Parker, J. M., D. Guo, and R. S. Hodges, *New hydrophilicity scale derived from high-performance liquid chromatography peptide retention data: correlation of predicted surface residues with antigenicity and X-ray-derived accessible sites*. Biochemistry, 1986. 25(19): p. 5425-32, Ponomarenko, J. V. and P. E. Bourne, *Antibody-protein interactions: benchmark datasets and prediction tools evaluation*. BMC Struct Biol, 2007. 7: p. 64). Certain amino acids occur more frequently in epitopes compared to others (Jin L et al., J Mol Biol. 1992, 226(3):851), and this is reflected in their Discotope LODrps values as illustrated in Table 1 (Haste Andersen, P, Protein Sci, 2006. 15(11): p. 2558-67).

Accordingly, x-HAs were generated by altering the steric shapes of primary antigenic determinants towards reducing their immunogenicity. Replacement amino acids are low or negative LODrps residues that occur rarely in stable antigen-antibody interfaces. Primary antigenic determinant ablation is performed by replacing primary antigenic determinant residues identified by the drift and escape mutant data of Table 2 with amino acids that have lower LODrps values according to the scheme detailed in Table 3. Reducing the tendency of antibodies to bind primary antigenic determinant sites by replacement of positive LODrps amino acids with low or negative LODrps amino acids should prevent clonal expansion of B-cells producing antibodies to the original primary antigenic determinants as well as the "knocked out" sites, and thereby facilitate expansion of B-cells making antibodies to conserved, normally "immunorecessive" sites on the hemagglutinin molecule that do not routinely elicit detectable immune responses.

During the design process, it is important to avoid changes that induce protein-folding problems in regions distal to the primary antigenic determinants, because these regions may contain structures that will become "secondary" epitopes. Therefore, modifications were limited to the confines of well-defined primary antigenic determinants. The x-HA.4 and xHA.5 variants, have all 5 primary antigenic determinants knocked out, but by different combinations of amino acid substitutions (right side of Table 3). In theory, ablation of all 5 epitopes should direct the immune response to conserved epitopes. In contrast, the x-HA.1, x-HA.2, and x-HA.3 hemagglutinins were designed to eliminate, as well as to retain, different subsets of primary antigenic determinants. These serve as experimental controls, but may also elicit immune responses to conserved epitopes.

For the x-HA.4 series, 6 high LODrps residues in the V1203 primary antigenic determinants were replaced with escape mutant residues in x-HA.4a, or mainly threonine (LODrps=−0.233) in x-HA.4b, or mainly alanine (LODrps=−1.522) in x-HA.4c. Based on detailed analysis of the 2FK0 trimer structure, escape mutant and drift data, modification of just 6 residues should completely ablate the HA primary antigenic determinants. x-HA.5 series hemagglutinins, with 10 changes in primary antigenic determinant residues should further eliminate residual antigenicity in the primary epitopes.

Note that 2 residues, which are understood to contribute to the primary antigenic determinants based on escape mutant data, were not altered. These are 1155, which already has a low LODrps value (−0.713), and D187, which is at the edge of the receptor binding domain (RBD). This decision was based on a D187 substitution perturbing the nearby RBD, and thereby disrupting sialic acid binding. The other reason for keeping the conserved D187 residue is that, by preserving the RBS, it is possible to generate an immune response against the RBS. Such an antibody would be an ideal neutralizing antibody as has been recently demonstrated (Whittle, J. R., R. Zhang, S. Khurana, L. R. King, J. Manischewitz, H. Golding, P. R. Dormitzer, B. F. Haynes, E. B. Walter, M. A. Moody, T. B. Kepler, H. X. Liao, and S. C. Harrison, *Broadly neutralizing human antibody that recognizes the receptor binding pocket of influenza virus hemagglutinin*. Proc Natl Acad Sci USA, 2011. 108(34): p. 14216-21).

In the bottom row of Table 3 a measurement called the LODrps index was introduced. It is calculated by summing the LODrps values for primary antigenic determinant residues of the HA in each column and serves as a relative indicator of the degree to which the primary antigenic determinants are neutralized in a given hemagglutinin molecule. The parental V1203 HA control has a LODrps index value of 6.7, which is similar to the 4.6 and 6.3 values obtained for the other naturally occurring Indo05 and Egypt06 control hemagglutinins. Partial neutralization of V1203 primary antigenic sites one mAb epitope at a time in x-HA.1, x-HA.2 and x-HA.3, modestly reduced the 6.7 index value to around 4. However, (almost) wholesale replacement of V1203 primary antigenic determinant residues with escape mutant substitutions in x-HA.em reduced the index value to 0.6. For the x-HA.4 series in which 6 primary epitope residues were substituted with escape mutant residues, threonine, or alanine, index values were 0.4, −3.2 and −9.6, respectively. For the x-HA.5 series, the index values were −9.2 and −15.6. The inventor hypothesizes that, by reducing the LODrps indices of x-HA mutants, modified surfaces of the HA becomes less antigenic, and thereby to switch the immune response to remaining higher LODrps residues of conserved HA surfaces that are not normally immunogenic.

Immunoassays Verify Proper Folding of Recombinant Hemagglutinins and Primary Antigenic Determinant Knock Out in xHAs Recombinant xHA protein folding was assessed by testing for binding to well-characterized mAbs which recognize discontinuous epitopes on the HA head and stem. Human mAb 1F02 recognizes the conserved fusion peptide-containing epitope on Group 1 HA stems and protects mice from in vivo virus challenge with antigenically distinct influenzas (Wrammert et al. J Exp Med, 2011. 208(1): p. 181-193). The VN04 mAbs recognize 3 discontinous epitopes, and 1 linear epitope, within the primary antigenic determinant surfaces of the V1203 HA (Kaverin et al., J Virol, 2007, 81:12911). Binding was assayed by immobilizing xHAs, or a control protein (human antithrombin III), at 1 ug/ml on microplates, followed by blocking and serial exposure to 1F02 and alkaline phosphatase—goat anti human Ig, or to the VN04 mAbs and alkaline phosphatase—goat anti mouse Ig. FIG. 5 shows that the 1F02 mAb to the HA stem epitope bound all of the xHAs, whereas the VN04 mAbs to V1203 primary antigenic determinants, bound to xHA.par (which has a wildtype HA head surface with intact primary antigenic determinants), but not xHA.4b and 5a (which have ablated immunodominant epitopes, see Table 3). Together, the binding data are supportive of proper folding of the xHA.par and the xHA.4b and 5a hemagglutinins, and also confirm successful knock-out of primary antigenic determinants in the latter.

Example 3 Production of Antisera to H5 Control and x-HA Hemagglutinins, Surrogate Assay for Viral Neutralization Function, and Identification of x-HA Universal Vaccine Candidates Overview The abilities of control and x-HA hemagglutinins to elicit broadly cross-protective humoral antibody responses were examined in mice. Antisera raised to individual control and x-HA hemagglutinins, as well as antisera raised by sequential challenge with different x-HAs, were screened in HA pseudotyped lentiviral vector reporter neutralization assays to identify molecules that stimulate responses to stable, conserved regions of H5 hemagglutinins.

Production of Mouse Antisera to Recombinant Hemagglutinins

Non-immune serum is collected from mice. Groups of 4 or 5 Balb/C or fVB mice are vaccinated by injection with 10 or 20 ug of a control or x-HA hemagglutinin in Sigma Adjuvant System (S6322, formerly Ribi Adjuvant System). Three weeks after the primary injection and at >21 day intervals after each boost, animals received additional 10 ug boosts. Blood was drawn 1-2 weeks after the booster immunizations. Mice are immunized with a single control or x-HA hemagglutinin repeatedly, or receive different x-HA antigens for the original immunization and subsequent boosts an alternative immunization protocol.

Characterization of x-HA Cross-Protective Function Using Influenza Hemagglutinin Pseudotyped Lentiviral Vector Reporter Assays If an x-HA is to serve as an effective avian influenza pandemic vaccine and antigen for immunotherapeutic development, it must elicit immune responses to hemagglutinins from a wide range of H5 influenzas independently of sharing primary antigenic determinants with evolving strains, and those immune responses must lead to the neutralization of viral function in order to achieve cross protection. A lentiviral vector reporter assay is used to quantify the ability of antisera raised against various control and x-HA hemagglutinins to inhibit HA-mediated membrane fusion, which is a essential step in the infection process and viral life cycle.

The HA pseudo virus lentiviral vector reporter assay was developed, and the components were generously provided, by Dr. Gary Nabel and colleagues from the NIH Vaccine Research Center (Kong, W. P., et al., *Protective immunity to lethal challenge of the 1918 pandemic influenza virus by vaccination.* Proc Natl Acad Sci USA, 2006. 103(43): p. 15987-91.). To generate the flu HA pseudotyped reporter viruses, 293T cells were cotransfected with 7 ug of pCMVΔR8.2, 7 ug of pHR'CMV-Luc, and 125 ng of a CMV/R 8κB H5 construct, wherein the HA segment corresponds to H5 A/Vietnam 1203/04 (clade 1), A/Thai1(KAN-1)/04 (clade 1), A/Indonesia/5/05 (clade 2.1.3), A/Egypt/2782/06 (clade 2.2), A/Nigeria/641/06 (clade 2.2), or A/Iraq/207/06 (clade 2.2). The packaging cells are transfected overnight, then changed to fresh medium. At 48 h, virion-containing supernatants were harvested, 0.45-um filtered, aliquoted, and used immediately, or frozen at −80° C.

For neutralization assays, antiserum dilutions are mixed with lentiviruses that have been pseudotyped with the different H5 hemagglutinins, then added to 96-well plates containing 5,000 293A cells per well. The medium is changed 14-16 h later, and at 72 or 96 h post infection, cells are lysed and the lysates assayed for luciferase activity (Promega Bright Glo assay). Percent neutralization of the LV reporters by tested antisera is calculated as {1−[(luminescence in wells with added antiserum)/(luminescence in wells with no added antiserum)]}. Lentivirus neutralization titers are obtained by analyzing neutralization as a function of antiserum dilution. For example, LVnt50 is the greatest antiserum dilution producing at least 50% inhibition of neutralization. The HA-pseudotyped LV reporter assay is used to screen antisera and identify xHAs inducing neutralizing antibodies to conserved HA features. The desired xHAs will elicit antisera with high titers for the neutralization of multiple HA pseudotypes. For the x-HA.4 and x-HA.5 series in which all primary antigenic determinants are knocked out and replaced in 4 out of 5 cases with very low LODrps amino acids, we predict that the immune response will be switched to substructures on the HA surface that are not normally immunogenic, and that if such substructures are conserved, the antisera will bind and neutralize reporter viruses pseudotyped for all the clades.

Targets of Antibodies to x-HA_s with Universal Vaccine Function

Epitope identification algorithms such as DiscoTope (Haste Andersen, P., M. Nielsen, and O. Lund, *Prediction of residues in discontinuous B-cell epitopes using protein 3D structures.* Protein Sci, 2006. 15(11): p. 2558-67) are used to predict the locations of the secondary antigenic determinants. On the right side of Table 2, residues of the A/Viet/1203/04 HA ectodomain that DiscoTope predicts to be epitopes are marked. The Discotope algorithm predicted 34 residues as epitopes. On the basis of genetic drift and escape mutant data, 12 of the 34 correspond to HA primary antigenic determinants. The remaining 18 residues, not mapped to known primary antigenic determinants, potentially include some conserved secondary antigenic determinants.

Conserved hemagglutinin structural features mediating viral functions whose interruption causes neutralization include: (1) sites in and bordering the receptor binding site, and (2) stem fusion peptide structural elements participating in the conformational change that mediates viral envelope fusion with the host cell membrane (Skehel, J. J. and D. C. Wiley, *Receptor binding and membrane fusion in virus entry: the influenza hemagglutinin.* Annu Rev Biochem, 2000. 69: p. 531-69.).

The inventor hypothesizes that (1) structural neutralization of HA primary antigenic determinants shifts the immune response towards conserved epitopes, and that (2) sequential immunization with different x-HAs (Table 5, lines 13 and 14) will be superior for eliciting broadly protective immune responses.

Example 4: Cross Neutralization Results

Table 4 shows experiments investigating neutralization of clade 1, clade 2.2 and clade 2.1.3 H5 HA-pseudotyped lentiviruses by antisera raised against recombinant xHA immunogens bearing intact wildtype (xHA.par), and partially (xHA.2) and completely (xHA.4b and xHA.5a) ablated primary antigenic determinants. Mouse non-immune sera did not neutralize any of the reporter viruses. Antisera generated with the V1203 xHA.par parental control exhibited a focused pattern of neutralization, which was limited to the V1203 clade 1 and Egypt clade 2.2 pseudotypes. Broader cross neutralization, extending to the H5 Indonesia clade 2.1 and H1 PR8 reporters, was obtained with antisera to xHA.2, which has partial ablation of hemagglutinin primary antigenic determinants. Additionally, antisera raised by priming with xHA.4b and subsequent xHA.5a boosting also produced broad cross neutralization. For reference, the neutralization pattern obtained with purified mAb 1F02 (Wrammert et al. J Exp Med, 2011. 208(1): p. 181-193) is shown in the Controls section at the bottom of the Table 4. The 1F02 mAb binds a conserved, fusion peptide-containing epitope on the HA stem and provides in vivo protection against several antigenically distinct influenzas when administered therapeutically. The broad in vitro neutralization observed with the polyclonal antisera from xHA immunized animals, may result from contributions of antibodies like 1F02, which recognize conserved elements on the HA stem, and/or from recently described antibodies to conserved elements on the HA head, which interfere with receptor binding.

The broadened neutralization results were obtained for a portion of the mice immunized with xHAs, indicating that ablation of primary epitopes can promote an immune response with potential to protect against different serovariants. Different adjuvant strategies may be applied to increase the reproducibility and magnitude of the response.

TABLE 4

BROADENED NEUTRALIZATION OF INFLUENZA HEMAGGLUTININ PSEUDOTYPED LENTIVIRUS REPORTERS BY xHA ANTISERA

| mouse ID | serum from[3] | LVNT50[1] V1203 H5 clade 1 | LVNT50 Indo H5 clade 2.1 | LVNT50 Egypt H5 clade 2.2 | LVNT40[2] PR8 H1 |
|---|---|---|---|---|---|
| non-immune serum; 2 BALB/c mice ||||||
| bD.LR | n.a. | 0 | 0 | 0 | 0 |
| bE.LR | n.a. | 0 | 0 | 0 | 0 |
| xHApar: 10 ug prime and boosts; 2 BALB/c mice ||||||
| bA.L | b2 | >912 | 0 | >3648 | 0 |
| bA.R | b3 | >1706 | 0 | >6823 | 0 |
| xHA.2: 20 ug prime and 10 ug boosts; best 2 of 3 BALB/c mice ||||||
| A4.0 | b6 | >5472 | 0 | >2736 | >342 |
| A4.L | b6 | >685 | 0 | >2742 | >1371 |
| xHA.2: 10 ug prime and boosts; best 2 of 5 BALB/c mice ||||||
| bB.LR | b4 | >3655 | 0 | >3655 | >114 |
| bB.R | b4 | >914 | >914 | >3655 | 0 |
| 20 ug xHA.4b prime and 10 ug xHA.50 boosts; best 3 of 4 BALB/c mice ||||||
| B2.0 | b7 | >914 | >228 | >3655 | >457 |
| B2.LR | b4 | 0 | 0 | >2742 | >343 |
| B2.R | b5 | 0 | 0 | >457 | >457 |
| 10 ug xHA.4b prime and 10 ug xHA.50 boosts; best 2 of 5 BALB/c mice ||||||
| bC.LR | b4 | 0 | >171 | >2742 | 0 |
| bC.R | b5 | >533 | >133 | >4265 | >133 |
| 10 ug xHA.4b prime and 10 ug xHA.5a boosts; best 2 of 4 fVB mice ||||||
| fC.L | b3 | >914 | >914 | >3655 | 0 |
| fC.LL | b5 | >685 | >685 | >5483 | >685 |
| CONTROLS ||||||
| mAb 1F02, 32 ug/ml | | >228 | 0 | >1824 | >114 |
| rabbit α H5N1 rgA/Viet/1203/04 (BEIR NR-4485) | | >22800 | 0 | >11400 | 0 |
| goat α H5 HAA/tern/South Africa/61 (BEIR NR-3156) | | >91200 | 0 | >18240 | 0 |
| goat α H1 HAA/Puerto Rico/8/1934 (BEIR NR-3148) | | 0 | 0 | 0 | >54825 |

[1] LVnt50, serum dilution producing >50% neutalization
[2] LVnt40, serum dilution producing >40% neutralization
[3] b2, boost 2; b3, boost 3; n.a., not applicable

Example 5: xHAs Elicit Antibodies to Conserved Fusion-Peptide Containing Epitopes on the HA Stem When administered therapeutically, monoclonal antibodies to conserved fusion peptide-containing epitopes on the hemagglutinin stem mediate broad influenza protection. Therefore, it is of interest to determine if xHAs elicit immune responses to the conserved stem epitopes and could be used to strengthen immunological memory for and induce production of broadly protective stem antibodies. Example 5 and FIG. 6 show that mouse immunization with xHAs elicits antibodies to this critical HA stem element.

Monoclonal antibody 1F02 binds to a conserved fusion peptide-containing epitope on Group 1 HA stems and protects mice from live virus challenge by antigenically distinct influenzas (Wrammert et al. J Exp Med, 2011. 208(1): p. 181-193). mAb 1F02 was used in a competition elisa to determine if antibodies to conserved fusion peptide-containing epitopes on the HA stem are present in polyclonal antisera from mice immunized with xHAs. The solid phase for the assay was BEIR NR-4143 rgA/Vietnam/1203/04 (H5N1) monovalent influenza sub□ virion vaccine, with its hemagglutinin element derived from V1203. NR-4143-coated wells were exposed to dilutions of anti-xHA mouse antisera, or to non-immune serum, or control mouse mAb C179 (Okuno, Y., Y. Isegawa, F. Sasao, and S. Ueda, A common neutralizing epitope conserved between the hemagglutinins of influenza A virus H1 and H2 strains. J Virol, 1993. 67(5): p. 25520 8) as negative and positive competition controls, respectively; followed by incubation with 1.2 ug/ml human mAb 1F02. 1F02 binding was measured with alkaline phosphatase goat anti-human Ig. Percent 1F02 binding values, calculated as (A405 in the presence of antiserum)/(A405 in the absence of antiserum), were used to assess the presence and level of stem fusion-peptide epitope binding antibodies in the serum samples.

Results of 1F02 competition experiments are presented in FIG. 6. Panel A shows no competition by mouse non-immune serum (m NI, open circles), and competitive, concentration-dependent reduction of 1F02 binding following exposure to the positive control C179 mAb (solid triangles). Each of the plots in the remaining B-D panels presents 1F02 competition results from serum samples obtained at various stages during the immunization of a single animal with xHAs. The designation "pr" indicates antisera obtained after priming, "b1" and "b2" are respectively antisera obtained after boosts 1 and 2, etc. The animals in panel B were primed and boosted with xHA.par (10 ug/injection). The animals in panels C and D, were primed with xHA.4b, then repeatedly boosted with xHA.5b; those in C received 10 ug doses of the xHA antigens, while those in D received 20 ug priming and 10 ug boosting doses.

Antisera obtained after priming did not contain measurable 1F02 competitive activity. But in the selected animals shown, 1F02-competing antibodies developed subsequently, appeared in sera collected after the first, second or third boost, and persisted once they had appeared. Surprisingly, anti-stem antibodies were present not only in xHA.4b-primed and xHA.5a-boosted mice (C and D), but also in animals challenged solely with wildtype xHA.par (B). Flu infections and seasonal vaccines are thought to elicit only limited production of anti-stem antibodies. However, the HA stem of the recombinant xHA.par immunogen, which is comprised of HA0 trimers and oligomers, may be more accessible than are HA stems contained in the virion envelope or vaccine preparations, which undergo formalin cross-linking during manufacture. Additionally, adjuvants expand and enhance antibody responses to influenza (Coler, R. N. et al., *A synthetic adjuvant to enhance and expand immune responses to influenza vaccines*. PLoS One, 2010. 5(10): p. e13677; Khurana, S., et al., *Vaccines with MF59 adjuvant expand the antibody repertoire to target protective sites of pandemic avian H5N1 influenza virus*. Sci Transl Med, 2010. 2(15): p. 15ra5.). Accordingly, adjuvanted (Sigma Adjuvant System) xHA.par administration may have been another factor in the production of anti-stem antibodies for this group.

Neutralization and 1F02 competition results were not tightly correlated, consistent with a polyclonal immune response to xHA antigens. The neutralization and 1F02 competition result disparities imply that antibodies to conserved structures above and beyond the fusion peptide-containing stem epitope also contribute to neutralization. These, for example, might include broadly neutralizing antibodies which bind to the HA head and inhibit RBS access.

Example 6: xHAs Elicit Antibodies to HA Head Epitopes

Hemagglutination inhibition (HAI) assays were performed to determine if xHAs induced antibodies that interfered with red blood cell (RBC) sialic acid binding to the HA receptor binding sites of three different H5 and one H1 hemagglutinin. Antigens were HA-pseudotyped lentiviruses of the specificity indicated by row labels. LVs were incubated for 30 min with dilutions of receptor destroying enzyme (RDE) treated antisera, or no serum, as indicated by column labels in panels B-D. Plates were photographed 40 m after turkey RBC addition. RBC buttons in the bottom right corner wells of each panel are RBC-only, no-hemagglutination controls. Clear appearance of the four wells above the no-hemagglutination controls indicates HAI by the respective LV antigens. Comparisons of the three left wells of bottom rows with adjacent no-hemagglutination control show that RDE-treated antisera had no inherent hemagglutinating activity. Presence of RBC buttons of various sizes in wells where antiserum was incubated with LV antigen indicates inhibition of hemagglutination by antibodies contained in the antiserum, and demonstrates that xHA immunization can induce production of antibodies that reduce interactions between HA head receptor binding sites and RBC sialic acids. Panel A shows controls for mouse (M) and rabbit (R, BEIR NR-4484) nonimmune (NI) sera, a polyclonal rabbit antiserum (BEIR NR-4487) to V1203, and a polyclonal goat antiserum (NR-3148) to PR8. Antisera for the panel B experiment were from mice primed and boosted with xHA.par (10 ug/injection). Antisera for the panel C experiment were from mice primed with xHA.4b, then boosted 4 times with xHA.5b using 10 ug of the xHA antigens. Antisera for the panel D experiment were from mice primed with xHA.4b, then boosted 6 times with xHA.5b (20 ug primes and 10 ug boosts).

Sera from mice immunized with the parental control xHA.par hemagglutinin bearing intact primary antigenic determinants produced expected inhibition of hemagglutination (panel A). Panels C and D show HAI results from animals primed with xHA.4b and boosted with xHA.5b. The primary antigenic determinants on xHA.4b and xHA.5a were ablated with different combinations of low LODrps amino acid substitutions (see Table 3 and FIG. 5). Hemagglutination inhibition was also noted for some anti-xHA.4b-5a antisera, indicating production of antibodies to secondary epitopes that are adjacent to the receptor binding site, or which alter the conformation of the RBS when the antibodies are bound. Thus, xHA.4b and xHA.5a, which have different primary antigenic determinant surfaces than the HAs on the conventional hemagglutinating antigens, can elicit antibodies to HA head region sites that are distinct from the primary antigenic determinants, but nevertheless reduce RBS access. Several antibodies to conserved epitopes on the HA head mediate broad influenza protection (Khurana et al., PLoS Med, 2009. 6(4): p. e1000049; Krause et al., J Virol, 2011. pmid_21849447; Whittle, et al., Proc Natl Acad Sci USA, 2011. 108(34): p. 1421621; Yoshida, et al., PLoS Pathog, 2009. 5(3): p. e1000350). The HA inhibition observed with xHA.4b-5a induced antibodies observed suggests that the receptor-binding inhibition

Example 7: xHA.5a Primary Antigenic Determinant Ablations Broaden Immune Response to H5 Influenzas

TABLE 5

| LVnt50 [1] titers from xHA.5a immunized mice | | | | | |
|---|---|---|---|---|---|
| MOUSE ANTISERA [2] | | HA-pseudotype of LV reporters | | | |
| immunogen | serum [3] | V1203 | indo | egypt | PR8 |
| xHA.par | b2 | >912 | o | >3648 | o |
| xHA.par | b3 | >1706 | o | >6823 | o |
| xHA.5a | b2 | o | o | >3648 | o |
| xHA.5a | b2 | >228 | o | >1824 | o |
| xHA.5a | b2 | >1824 | >456 | >3648 | o |
| xHA.5a | b2 | >912 | >228 | >3648 | o |
| none | n.a. | o | o | o | o |
| none | n.a. | o | o | o | o |
| none | n.a. | o | o | o | o |
| CONTROLS | | | | | |
| goat anti H5 HA A/tern/South Africa/61 (BEIR NR-3156) | | >91200 | o | >182400 | o |
| rabbit anti H5N1 rgA/Viet/1203/04 (BEIR NR-4485) | | >22800 | o | >11400 | o |
| mAb 1F02, 56 ug/ml | | >456 | o | >3648 | >114 |

[1] LVnt50, serum dilution producing >50% neutralization
[2] each row is a different mouse
[3] b2, boost 2; b3, boost 3; n.a., not applicable Table 5 shows that mice challenged with xHA.5a, an H5 A/Viet/1203/2004-derived hemagglutinin with knock out of all primary antigenic determinants (see Table 3 and FIG. 5), produced polyclonal antisera with broader H5 neutralization than did mice challenged with the parental xHA.par control hemagglutinin, which retains the intact, wild type primary antigenic determinants of V1203. Given that the V1203 primary antigenic determinants were not present on the xHA.5a immunogen, it is likely that the broadly neutralizing antibodies it elicited in 2 mice recognize H5 structural elements that are well-conserved across the H5 subtype. The significance of Example 7 is that it demonstrates that a response can be elicted with only one xHA. This suggests that a broadly protective vaccine against circulating and future pandemic H5 avian influenzas could be developed from an xHA.5a platform.

The foregoing examples demonstrate that xHAs are properly folded and form the correct prefusion trimeric form, and therefore present as many of the conserved epitopes as possible, including epitopes that have not been identified. These xHAs elicit POLYCLONAL responses containing antibodies to a variety of different conserved HA structures, each of which mediate distinct essential functions in the virus life cycle. For example, the combined presence of (a) antibodies to conserved epitopes on the head and (b) antibodies to conserved stem epitopes would block virus replication at 2 different points in the life cycle (infection and fusion), which are more effective than blocking either step alone.

The reported xHA approach is fundamentally different from widely proposed universal flu vaccine development strategies of isolating broadly neutralizing mAbs, precisely mapping their epitopes, and using this information for structure-based design of immunogens that will elicit antibodies focused around the mapped epitope. Instead, xHAs are 'generic' hemagglutinin molecules, which have knocked-out immunodominant epitopes, but retain normal overall HA tertiary and quartenary structure, including multiple conserved elements shared by distantly related influenzas. In contrast to peptide-based and truncated HA universal vaccine candidates, trimeric xHAs provided a single immunogen to elicit antibodies to multiple conserved epitopes, leading to polyclonal anti-xHA antisera containing antibodies to conserved, neutralization-mediating HA stem and head targets. This finding supports the feasibility of developing long-lasting, broadly neutralizing, subunit-type universal flu vaccines from an xHA platform. xHA vaccines are also suitable for both stimulating and amplifying "seasoned" pan-influenza immunity, wherein cross-protection is mediated by the combined effects of complementary, broadly neutralizing antibodies. This represents a promising development because it means that xHA-based universal flu vaccines should be able to work in adults through a mechanism of boosting conserved epitope memory cells, rather than priming.

What is claimed is:

1. A method of reducing the immune response to a primary immunodominant epitope on a protein antigen while retaining overall protein structure, comprising:
   (a) identifying one or more primary antigenic amino acids of the primary immunodominant epitope of the protein antigen having a high log odds relative propensity scale (LODrps) value, wherein identifying one or more primary antigenic residues of the primary immunodominant epitope of the protein antigen comprises:
      comparing the amino acid sequence of the protein antigen to a corresponding amino acid sequence of at least one of an escape mutant and a genetic drift isolate; and
      identifying one or more amino acids that differ between the amino acid sequence of the protein antigen and the amino acid sequence of the at least one of the escape mutant and the genetic drift isolate; and
   (b) replacing at least one of the one or more amino acids having the high LODrps value with an amino acid having a low LODrps value such that overall protein structure of the protein antigen is retained.

2. The method of claim 1, wherein the amino acid having a low LODrps value is alanine or threonine.

3. A method of making a vaccine that elicits an immune response against non-immunodominant conserved epitopes on a protein antigen, comprising:
   (a) identifying one or more primary antigenic residues of a primary immunodominant epitope of the protein antigen, wherein identifying one or more primary antigenic residues of the primary immunodominant epitope of the protein antigen comprises:
      comparing the amino acid sequence of the protein antigen to a corresponding amino acid sequence of at least one of an escape mutant and a genetic drift isolate; and
      identifying one or more amino acids that differ between the amino acid sequence of the protein antigen and the amino acid sequence of the at least one of the escape mutant and the genetic drift isolate;
   (b) determining the log odds relative propensity scale (LODrps) value of the one or more primary antigenic residues;
   (c) replacing at least one of the one or more primary antigenic residues having a high LODrps value with an amino acid having a low LODrps value to generate a modified protein antigen having reduced antigenicity and retained overall protein structure of the protein antigen; and
   (d) utilizing the modified protein antigen to induce antibodies against the non-immunodominant conserved epitopes.

4. The method of claim 3, wherein each of the primary antigenic determinant residues having a high LODrps value is replaced with an amino acid having a low LODrps value.

5. The method of claim 3, wherein the protein antigen is a surface haemagglutinin (HA) from Influenza A.

6. The method of claim 5, wherein the surface HA from Influenza A is an H5 HA.

7. The method of claim 1, wherein the protein antigen is a surface haemagglutinin (HA) from Influenza A.

8. The method of claim 7, wherein the surface HA from Influenza A is an H5 HA.

9. The method of claim 1, wherein each of the one more primary antigenic amino acids having the high LODrps value is replaced with an amino acid having a low LODrps value.

10. The method of claim 1, wherein the high LODrps value is greater than about 0.3.

11. The method of claim 3, wherein the step of identifying one or more primary antigenic residues of the primary immunodominant epitope of the protein antigen comprises the steps of:
   comparing the amino acid sequence of the protein antigen to a corresponding amino acid sequence of each of an escape mutant and a genetic drift isolate; and
   identifying one or more amino acids that differ between the amino acid sequence of the protein antigen and the amino acid sequence of each of the escape mutant and the genetic drift isolate.

12. The method of claim 3, wherein the amino acid having a low LODrps value is alanine or threonine.

13. The method of claim 3, wherein the high LODrps value is greater than about 0.3.

14. The method of claim 6, wherein the primary immunodominant epitope comprises amino acids 138-209 of SEQ ID NO:1.

15. The method of claim 1, wherein the step of identifying one or more primary antigenic residues of the primary immunodominant epitope of the protein antigen comprises the steps of:
   comparing the amino acid sequence of the protein antigen to a corresponding amino acid sequence of each of an escape mutant and a genetic drift isolate; and
   identifying one or more amino acids that differ between the amino acid sequence of the protein antigen and the amino acid sequence of each of the escape mutant and the genetic drift isolate.

* * * * *